United States Patent [19]

Kramer et al.

[11] 3,932,487
[45] Jan. 13, 1976

[54] 13-SULFA-PROSTAGLANDINS

[75] Inventors: Josef Kramer; Hans Radunz; Dieter Orth; Manfred Baumgarth; Jurgen Harting, all of Darmstadt, Germany

[73] Assignee: Merck Patent Gesellschaft mit beschrankter Haftung, Darmstadt, Germany

[22] Filed: Nov. 15, 1973

[21] Appl. No.: 416,183

[30] Foreign Application Priority Data
Nov. 17, 1972 Germany............................ 2256537

[52] U.S. Cl............ 260/468 D; 260/340.9; 260/399; 260/456 P; 260/464; 260/470; 260/485 R; 260/514 D; 260/516; 260/557 R; 260/609 R; 260/609 F; 424/305; 424/317
[51] Int. Cl.$^2$................ C07C 149/26; C07C 149/40
[58] Field of Search..................... 260/408 D, 514 D

[56] References Cited
UNITED STATES PATENTS
3,749,741 7/1973 Strike et al. ..................... 260/345.7
3,776,940 12/1973 Just et al............................ 260/468

OTHER PUBLICATIONS
Fried et al., Ann. N.Y. Acad. Sci., 180, 38 (1971).
Schaf et al., J. OC., 37, 2921 (1972).
Nakano, Prostaglandins, pp. 21–28 (1973).

*Primary Examiner*—Robert Gerstl
*Attorney, Agent, or Firm*—Millen, Raptes & White

[57] ABSTRACT

Sulfides of the general formula

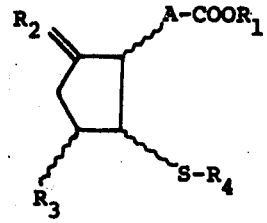

wherein $R_1$ is H or alkyl, $R_2$ is =O, (H,OH), or (H,lower-acyloxy), $R_3$ is H, OH or lower-acyloxy, $R_4$ is alkyl or alkyl substituted by F, OH, lower-acyloxy, phenyl or p-tolyl, and A is alkylene which can be mono- or polysubstituted by F, and the physiologically acceptable salts thereof, possess, in addition to a blood-pressure-lowering activity, prostaglandin-type and antiprostaglandin-type effects.

19 Claims, No Drawings

13-SULFA-PROSTAGLANDINS

BACKGROUND OF THE INVENTION

This invention relates to novel sulfides.

SUMMARY OF THE INVENTION

The compounds of this invention are sulfides of the general Formula I

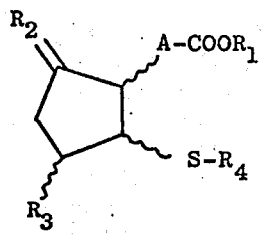

I wherein $R_1$ is H or alkyl of up to 12 carbon atoms; $R_2$ is =O, (H, OH), or (H, acyloxy of up to 4 carbon atoms); $R_3$ is H, OH, or acyloxy of up to 4 carbon atoms; $R_4$ is alkyl of up to 12 carbon atoms, unsubstituted or substituted by F, OH, acyloxy of up to 4 carbon atoms, phenyl or p-tolyl; and A is alkylene of up to 8 carbon atoms, unsubstituted or mono- or polysubstituted by F; and the physiologically acceptable salts thereof.

DETAILED DISCUSSION

In Formula I and the other formulae hereinafter, the bonds characterized by ∼∼∼ indicate either the α- or β-configuration, or both, i.e., a mixture of the compounds having opposite configurations.

The compounds of Formula I possess, with good physiological compatibility, blood-pressure-lowering activity. In addition, they possess prostaglandin-type and antiprostaglandin-type effects.

A compound of formula I showing weak prostaglandin-type effects can act in addition as a competitive inhibitor for prostaglandin and therefore may possess antiprostaglandine-type effects too.

Thus, the compounds possess vasodilatory, antiphlogistic, and diuretic properties. They also relieve bronchial spasm, inhibit the secretion of gastric juice, the aggregation of thrombocytes, lipid breakdown, and the liberation of noradrenalin, and reduce the swelling of the nasal mucous membrane. Furthermore, the compounds favorably affect the function of the corpus luteum, the transport of the ovum through the fallopian tube, nidation, and male fertility. Therefore, the compounds of Formula I can be employed as drugs, and also as intermediates for the preparation of other drugs.

The compounds of Formula I contain at least two asymmetrical C-atoms in the five-membered ring. When $R_2$ is other than =O or $R_3$ is other than H, then a third C-atom in the ring is also asymmetrical. When $R_2$ is other than =O and $R_3$ is other than H, then there are four centers of asymmetry in the ring. When A and/or $R_4$ are substituted and/or branched alkylene and/or alkyl, respectively, then additional centers of asymmetry can occur in the two side chains.

Therefore, the compounds of Formula I can occur in a plurality of stereoisomeric forms and are normally present as mixtures of racemates. If desired, each of the racemates can be isolated by conventional chemical/-physical methods.

The products of the process also comprise the optically active isomers of Formula I, as well as the racemates thereof. Especially preferred are the optically active stereoisomers of Formulae Ia - Ih, and their optical antipodes and racemates:

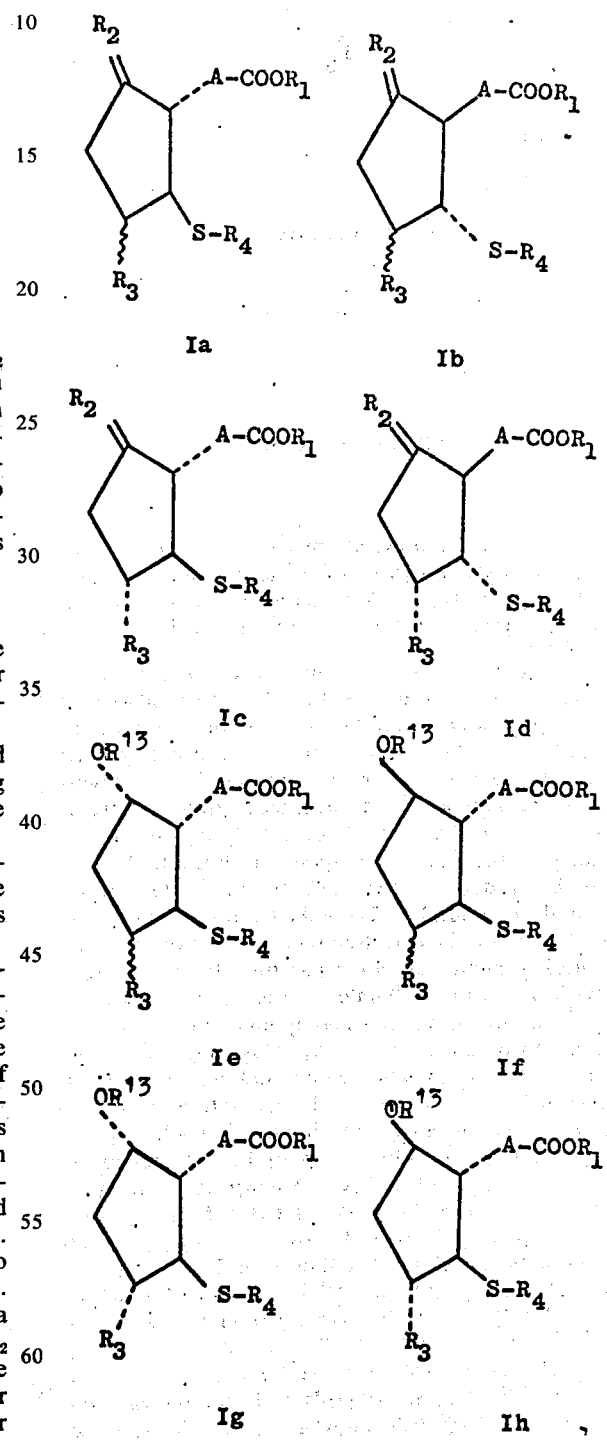

wherein $R_{13}$ is H or acyl of up to 4 carbon atoms.

In its process aspect, this invention relates to a process for the preparation of the compounds of general Formula I which comprises reacting a compound of the general Formula II

wherein D is

or

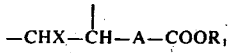

and X is Cl, Br, I, alkylsulfonyloxy of up to 4 carbon atoms, or arylsulfonyloxy of up to 10 carbon atoms, and $R_1$, $R_2$, and $R_3$ and A have the values given above, with a compound of the general Formula III $$W\text{-}S\text{-}R_4 \qquad \text{III}$$

wherein W is H or an equivalent of an alkali metal or alkaline earth atom; $R_4$ has the values given above; or liberating, in a compound otherwise corresponding to Formula I but wherein the hydroxy and/or keto groups and/or the carboxyl groups present therein are present in a functionally modified form, these groups by treatment with solvolyzing or hydrogenolyzing agents; or treating a thus-obtained compound of Formula I ($R_2$ = O) with a reducing agent; and/or converting a thus-obtained compound of Formula I into another compound of Formula I by treatment with esterifying or solvolyzing agents; and/or separating a compound of Formula I into the racemates and/or optical antipodes thereof; and/or converting a compound of Formula I by treatment with a base into a physiologically acceptable salt thereof; or liberating a compound of formula I out of their salts by treatment of the salt with an acid.

In the above formulae, in addition to being hydrogen, $R_1$ is preferably an alkyl of up to 12 carbon atoms, preferably straight-chain alkyl and especially those of up to 6 carbon atoms, e.g., methyl, ethyl, n-propyl, n-butyl, n-pentyl, n-hexyl, but also isopropyl, isobutyl, sec.-butyl, tert.-butyl, isopentyl, pent-2-yl, pent-3-yl, tert.-pentyl, neopentyl, hex-2-yl, hex-3-yl and isohexyl. Others include n-heptyl, n-octyl, n-nonyl, n-decyl, n-undecyl and n-dodecyl.

$R_2$ in addition to =O, also is (H, OH) and (H, acyloxy of up to 4 carbon atoms), preferably (H, OH), wherein the OH and/or the acyloxy group can be in the α- or β-position, or both, in the case of racemic mixtures. When $R_2$ is acyloxy, the acyl group is preferably that of a carboxylic acid, especially an alkanoic acid. Examples of such preferred acyloxy groups are formyloxy, acetoxy, propionyloxy, or butyryloxy groups. However the acyl group can be that of any simple acid, for example, from sulfonic acids and inorganic acids. Thus, in addition to alkanoyloxy, the acyloxy group can be, for example, a methylsulfonyloxy, ethylsulfonyloxy, and other alkanesulfonyloxy groups, e.g., 2-hydroxyethylsulfonyloxy, $HOSO_2O\text{-}$ or $(HO)_2P(O)\text{-}O\text{-}$ and other inorganic ester groups, e.g., of a molecular weight of up to 150.

$R_3$ in addition to H or OH, can also be an acyloxy group of up to 4 carbon atoms as defined for $R_2$. The OH or acyloxy group can be in the α- or β-position. When $R_2$ is (H, acyloxy of up to 4 carbon atoms) and $R_3$ is acyloxy of up to 4 carbon atoms, the acyloxy groups are preferably identical.

$R_4$ is straight-chain or branched alkyl of up to 12 carbon atoms, optionally mono- or polysubstituted by F, OH, acyloxy of up to 4 carbon atoms as defined above for $R_2$, phenyl or p-tolyl. Preferred straight-chain alkyl groups are methyl, ethyl, propyl, butyl, pentyl, hexyl, heptyl, octyl, nonyl and decyl and preferred branched chain alkyl are 2,2-dimethylpropyl, 3,3-dimethylbutyl, 4,4-dimethylpentyl, 5,5-dimethylhexyl, 6,6-dimethylheptyl, 7,7-dimethyloctyl, 8,8-dimethylnonyl, 9,9-dimethyldecyl. Other alkyl groups include isopropyl, isobutyl, isopentyl, isohexyl, isoheptyl, isooctyl, 2-butyl, 2-pentyl, 2-hexyl, 2-heptyl, or 2-octyl. Especially preferred are 3,3-dimethylpentyl, 3,3-dimethylhexyl, 3,3-dimethylheptyl, 3,3-dimethyloctyl and 3,3-dimethylnonyl.

Also especially preferred are alkyl groups substituted in the 2-position by OH or acyloxy of up to 4 carbon atoms, e.g., 2-hydroxypropyl, 2-hydroxybutyl, 2-hydroxypentyl, 2-hydroxyhexyl, 2-hydroxyheptyl, 2-hydroxyoctyl, 2-hydroxy-6,6-dimethylheptyl, 2-hydroxy-2-methylheptyl, 2-hydroxy-7,7-dimethyloctyl, 2-formyloxypropyl, 2-formyloxyheptyl, 2-acetoxyheptyl, 2-acetoxy-6,6-dimethylheptyl, 2-acetoxy-7,7-dimethyloctyl, 2-hydroxynonyl, 2-hydroxy-2-methylnonyl, 2-hydroxy-3,3-dimethylnonyl, 2-hydroxy-8,8-dimethylnonyl and the above-enumerated alkyl groups, substituted by OH in the 2-position.

$R_4$ can also be alkyl of up to 12 carbon atoms substituted by F, preferably a terminal-positioned trifluoroalkyl, e.g., 5,5,5-trifluoropentyl, 6,6,6-trifluorohexyl, 7,7,7-trifluoroheptyl, or 8,8,8-trifluorooctyl. When $R_4$ is phenyl-substituted alkyl, it preferably is an ω-phenylalkyl group, e.g., 3-phenylpropyl, 4-phenylbutyl, 5-phenylpentyl, 6-phenylhexyl, 7-phenylheptyl and 8-phenyloctyl. $R_4$ can also be p-tolyl-substituted alkyl, which also preferably is an ω-p-tolyl-alkyl group, e.g., 2-p-tolylethyl, 3-p-tolylpropyl and 4-p-tolylbutyl. Especially preferred are those aryl-substituted alkyl groups when substituted by OH in the 2-position.

$R_4$ can also be a polysubstituted alkyl residue of up to 12 carbon atoms, especially substituted by OH in the 2-position and phenyl or p-tolyl or fluorine in the ω-position. Especially preferred are 2-hydroxy-ω-p-tolylalkyl- and 2-hydroxy-2-methyl-ω-p-tolylalkyl-groups such as 2-hydroxy-2-p-tolylethyl-, 2-hydroxy-2-methyl-2-p-tolylethyl-, 2-hydroxy-3-p-tolylpropyl-, 2-hydroxy-3-p-tolylpropyl-, 2-hydroxy-2-methyl-3-p-tolylpropyl-, 2-hydroxy-4-p-tolylbutyl-, and 2-hydroxy-2-methyl-4-p-tolylbutyl-groups.

A is preferably unsubstituted alkylene of up to 8 carbon atoms, e.g., methylene, ethylene, trimethylene, tetramethylene, pentamethylene, hexamethylene, heptamethylene and octamethylene. A can also be alkylene of up to 8 carbon atoms substituted by F, i.e., a fluoroalkylene group, e.g., $\text{-}CH_2CHF\text{-}$, $\text{-}CH_2CF_2\text{-}$, -CH₂CH₂CHFCH₂-,   -CH₂CH₂CH₂CF₂-,
-CH₂CH₂CH₂CHFCHF-,   -CH₂CH₂CF₂-,
-CH₂CH₂CH₂CF₂CH₂-,   -CH₂CH₂CF₂CH₂CH₂-,
-CH₂CH₂CH₂CF₂CH₂CH₂-,   -(CH₂)₅CF₂- and
-(CH₂)₄CHFCHF-.

In Formula II, D is straight-chain ω-hydroxycarbonyl-1-alkenylene-(1,2) or ω-alkoxycarbonyl-1-alkenylene-(1,2), which optionally is mono- or polysubstituted by F; or straight-chain ω-hydroxycarbonyl-1-haloalkylene-(1,2) or ω-alkoxycarbonyl-1-haloalkylene-(1,2), also optionally mono- or polysubstituted by F, or the corresponding 1-alkylsulfonyloxy or 1-arylsulfonyloxy group. Examples for such D groups are:

7-hydroxycarbonyl-1-heptenylene-(1,2),
8-hydroxycarbonyl-1-octenylene-(1,2),
9-hydroxycarbonyl-1-nonenylene-(1,2),
7-ethoxycarbonyl-1-heptenylene-(1,2),
8-ethoxycarbonyl-1-octenylene-(1,2),
9-ethoxycarbonyl-1-nonenylene-(1,2),
1-chloro-8-hydroxycarbonyl-octylene-(1,2),
1-bromo-8-hydroxycarbonyl-octylene-(1,2),
1-iodo-8-hydroxycarbonyl-octylene-(1,2),
1-chloro-8-methoxycarbonyl-octylene-(1,2),
1-bromo-8-methoxycarbonyl-octylene-(1,2),
1-iodo-8-methoxycarbonyl-octylene-(1,2),
1-methylsulfonyloxy-8-ethoxycarbonyl-octylene-(1,2),
1-ethylsulfonyloxy-8-ethoxycarbonyl-octylene-(1,2),
1-p-tolylsulfonyloxy-8-ethoxycarbonyl-octylene-(1,2),
1-(4-bromophenyl)-sulfonyloxy-8-ethoxycarbonyloctylene-(1,2), and
1-α-naphthylsulfonyloxy-8-ethoxycarbonyl-octylene-(1,2).

When D is a group containing X, X in addition to Cl, Br, or I, also is alkylsulfonyloxy of up to 4 carbon atoms, preferably methylsulfonyloxy or ethylsulfonyloxy, or 2-hydroxyethylsulfonyloxy or butylsulfonyloxy; or arylsulfonyloxy of up to 10 carbon atoms, e.g., p-tolylsulfonyloxy, p-bromophenylsulfonyloxy, 1-naphthylsulfonyloxy and 2-naphthylsulfonyloxy.

W, in addition to H, can also be an equivalent of an alkali metal or alkaline earth atom, preferably Na, K or ½ Ca.

Accordingly, the compounds of Formula II comprise substituted cyclopentanones, 2-cyclopentenones, cyclopentanols and 2-cyclopentenols, which preferably are 3-halocyclopentanones, 3-alkylsulfonyloxycyclopentanones and 3-arylsulfonyloxycyclopentanones, especially 3-chloro-2-omega-carboxyalkyl-, 3-bromo-2-omega-carboxyalkyl-, 3-iodo-2-omega-carboxyalkyl-, 3-methylsulfonyloxy-2-omega-carboxyalkyl-, 3-p-tolylsulfonyloxy-2-omegacarboxyalkyl-, 3-bromo-4α-hydroxy-2-omega-carboxyalkyl-, 3-bromo-4β-hydroxy-2-omega-carboxyalkyl-cyclopentanones; 2-carboxyalkyl- and 2-carbalkoxyalkyl-2-cyclopentenones, especially 2-omega-carboxyalkyl-, 2-omega-carbalkoxyalkyl-, 4α-hydroxy-2-omega-carboxyalkyl, 4α-hydroxy-2-omega-carbalkoxyalkyl-, 4α-acyloxy-2-omega-carboxyalkyl-, 4α-acyloxy-2-omega-carbalkoxyalkyl-, 4β-hydroxy-2-omega-carboxyalkyl-, 4β-hydroxy-2-omega-carbalkoxyalkyl-, 4β-acyloxy-2-omega-carboxyalkyl-, 4β-acyloxy-2-omega-carbalkoxyalkyl-2-cyclopentenones; 3-halocyclopentanols, 3-alkylsulfonyloxycyclopentanols and 3-arylsulfonyloxycyclopentanols, especially 3-chloro-2-omega-carboxyalkyl-, 3-bromo-2-omega-carboxyalkyl-, 3-iodo-2-omega-carboxyalkyl-, 3-methylsulfonyloxy-2-omega-carboxyalkyl-, 3-p-tolylsulfonyloxy-2-omega-carboxyalkyl-, 3-bromo-4-hydroxy-2-omega-carboxyalkyl-, 3-iodo-4-hydroxy-2-omega-carboxyalkyl-cyclopentanols; 2-carboxyalkyl- and 2-carbalkoxyalkyl-2-cyclopentenols, especially 2-omega-carboxyalkyl-, 2-omega-carbalkoxyalkyl-, 4α-hydroxy-2-omega-carboxyalkyl-, 4α-hydroxy-2-omega-carbalkoxyalkyl-, 4α-acyloxy-2-omega-carboxyalkyl-, 4α-acyloxy-2-omega-carbalkoxyalkyl-, 4β-hydroxy-2-omega-carboxyalkyl-, 4β-hydroxy-carbalkoxyalkyl-, 4β-acyloxy-2-omega-carboxyalkyl- and 4β-acyloxy-2-omega-carbalkoxyalkyl-2-cyclopentenols.

The compounds of Formula III are optionally substituted thiols or alkali metal or alkaline earth thiolates, preferably n-alkyl- or 2-hydroxy-n-alkylthiols and/or the alkali salts thereof, especially optionally substituted n-propyl-, n-hexyl-, n-heptyl-, n-octyl-, 2-hydroxy-n-hexyl-, 2-hydroxy-n-heptyl-, 2-hydroxy-n-octyl- thiols and the corresponding sodium thiolates.

The compounds of Formula II are known or can be produced from known compounds in accordance with conventional processes.

For example, the diethylacetal of 2-bromo-2-cyclopentenone can be prepared therefrom in a conventional method by reaction with ethanol. This product, after treatment with lithium in ether, is reacted with [(CH₃O)₃P]₂CuI, and the thus-obtained organocopper compound is reacted, for example, with an omega-tert.-butoxycarbonyl alkyl iodide. This sequence of reactions is preferably conducted at between −50° and +5°, especially between −30° and −10°, and under an inert gas atmosphere, e.g., argon. However, it is also possible, for example, to react the cyclopentanone-2-carboxylic acid ester in a conventional manner with an omega-alkoxycarbonyl bromide or iodide or omega-cyanoalkyl bromide or iodide in the presence of an alkali metal alcoholate, e.g., NaOC₂H₅, then brominate the reaction product in an inert solvent, preferably a chlorinated hydrocarbon, such as CCl₄, with Br₂, and thereafter treat the product with H₂SO₄. In this process, a compound of Formula II is formed. The reaction mechanism by which this occurs is not fully understood.

The compounds of Formula III are known or can be prepared according to conventional methods, as they are described, for example, in HOUBEN-WEYL, "Methods of Organic Chemistry," Vol. IX, pp. 3 et seq., Stuttgart, 1955. Preferably, the starting materials are compounds otherwise corresponding to Formula III wherein W has the values given for X, preferably Br, and the reaction is accomplished with an alkali metal hydrogen sulfide, preferably KHS or NaHS. The reaction in most cases is in a solvent, preferably an alcohol, e.g., methanol, ethanol and isopropanol, optionally also in the presence of water or an aprotically dipolar solvent, e.g., acetone, dimethylformamide, dimethylsulfoxide, tetramethylurea, hexamethylphosphoric triamide, tetrahydrothiophene S,S-dioxide, ethylene carbonate, propylene carbonate and mixtures of such solvents. If the reaction mixture is worked up under acidic conditions, the free thiols of Formula III are usually obtained, which can be converted into the thiolates of Formula III by reaction with a base, preferably an alkali metal or alkaline earth metal hydroxides, especially NaOH and KOH.

The 2-hydroxyalkenethiols of Formula III are preferably produced from the corresponding 1,2-epoxyalkanes and H₂S in the presence of a basic catalyst.

The reaction of a compound of Formula II wherein D is

with a compound of Formula III takes place normally in the presence of a basic catalyst, using a suitable solvent, preferably an alcohol, e.g., methanol or ethanol. However, it is also possible, for example, to employ a hydrocarbon, e.g., benzene or toluene, as well as $H_2O$ or liquid ammonia, or to operate without solvent.

Suitable basic catalysts are preferably metal hydroxides, especially alkali metal and alkaline earth metal hydroxides, e.g., NaOH, KOH and $Ca(OH)_2$; alkali metal alcoholates, e.g., $NaOCH_3$, $NaOC_2H_5$ and K-tert.-$C_4H_9$; basic salts, preferably carbonates or acetates, e.g., $K_2CO_3$ and $NaOCOCH_3$; ammonia; amines, e.g., trimethylamine, triethylamine, isopropylamine, tert.-butylamine and ethylenediamine; alicyclic amines, e.g., cyclohexylamine, dicyclohexylamine and dimethylaniline; and heterocyclic amines, e.g., piperidine, pyrrolidine, pyridine, quinoline, diazabicyclo[2,2,2]-octane and diazabicyclo[3,4,0]-nonene; and quaternary ammonium hydroxides, e.g., tetramethylammonium hydroxide and benzyltrimethylammonium hydroxide.

The presence of such a basic catalyst is especially advantageous when a compound of Formula III wherein W is H is utilized. When employing a compound of Formula III wherein W is an equivalent of an alkali metal or alkaline earth metal atom, then the reaction mixture normally already is alkaline, so that the addition of a basic catalyst is unnecessary. It is, of course, also possible to use a basic catalyst, particularly liquid ammonia, as the solvent.

The process is conducted at −40° to 120°, preferably from room temperature to the boiling point of the reaction mixture. Reaction times normally range between about 3 hours and 7 days, depending on the reaction conditions, but longer or shorter times are possible.

The reaction of a compound of Formula II wherein D is

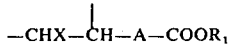

with a compound of Formula III wherein W is an equivalent of an alkali or alkaline earth atom takes place in a conventional manner described in detail in the literature. Preferably, the reaction is effected in an inert solvent, especially one of those mentioned above. The reaction temperatures range preferably between 0° and 120°, particularly from room temperature to the boiling point of the reaction mixture. Here again, the reaction times range usually between 3 hours and 7 days, depending on the reaction conditions.

The compounds of Formula I ($R^2 = 0$) are converted into the compounds of Formula I ($R_2 = $ [H, OH] and $R_3 = $ H or $R_2 = $ [H, OH] and $R_3 = $ OH) by treatment with a reducing agent which will leave the carboxyl group or the carbalkoxy group unchanged, i.e., preferably complex metal hydrides, particularly $NaBH_4$, optionally in the presence of $AlCl_3$ or LiBr, or $LiBH_4$. The reaction is advantageously accomplished in the presence of an inert solvent, e.g., a lower alcohol, or an ether, e.g., tetrahydrofuran or ethylene glycol dimethyl ether. The reaction is suitably completed by refluxing the reaction mixture. The thus-formed metal complexes can be decomposed in the usual manner, for example with an aqueous solution of ammonium chloride.

Under appropriate reaction conditions, the reduction can also be accomplished with chemically activated hydrogen. Thus, a selective reduction of the carbonyl group is possible, for example, by agitation with zinc dust in 50% strength acetic acid at 0°. Further suitable reducing agents are aluminum alcoholates, e.g., aluminum isopropylate (according to the method of Meerwein-Ponndorf, e.g., in benzene or toluene at temperatures of between about 20° and about 110°).

From other compounds of Formula I, esters of Formula I ($R_1 = $ alkyl of up to 12 carbon atoms) can be produced in accordance with methods described in the literature. Thus, an acid of Formula I ($R_1 = $ H) can be reacted, for example, with the respective alcohol in the presence of an inorganic or organic acid, e.g., HCl, HBr, HI, $H_2SO_4$, $H_3PO_4$, trifluoroacetic acid, a sulfonic acid, such as benzenesulfonic acid or p-toluenesulfonic acid, or an acidic ion exchanger, optionally in the presence of an inert solvent, e.g., benzene, toluene or xylene, at a temperature of between about 0° and preferably the boiling temperature. The alcohol is preferably used in an excess. Preferred alcohols are those of the formula $R_5OH$ wherein $R_5$ is alkyl of up to 12 carbon atoms. Examples of suitable alcohols are unbranched primary alcohols of up to 12 carbon atoms, e.g., methanol, ethanol, propanol, butanol, hexanol, octanol, decanol and dodecanol. Also suitable are, for example, isopropyl alcohol, sec.-butyl alcohol and tert.-butyl alcohol.

Additionally, the reaction can be effected in the presence of a water-binding agent, e.g., anhydrous heavy metal sulfates, or in the presence of a molecular sieve. The water of reaction can also be removed azeotropically wherein, advantageously, a hydrocarbon, e.g., benzene or toluene, or a chlorinated hydrocarbon, e.g., chloroform of 1,2-dichloroethane, is added. The esterification takes place under gentle conditions, if the water of reaction is chamically bound, by adding a carbodiimide, e.g., N,N'-dicyclohexylcarbodiimide, employing an inert solvent, e.g., ether, dioxane, 1,2-dimethoxy-ethane, benzene, $CH_2Cl_2$ and $CHCl_3$, and a base, e.g., pyridine, can be added. The methyl and ethyl esters, respectively, can also be prepared by reacting the free acids with diazomethane and diazoethane, respectively, in an inert solvent, e.g., ether, benzene and methanol. Also, esters of Formula I ($R_1$ is not H) can be obtained by chemically adding a carboxylic acid (I, $R_1 = $ H) to an olefin, e.g., isobutylene, preferably in the presence of a catalyst, e.g., $ZnCl_2$, $BF_3$, $H_2SO_4$, arylsulfonic acids, pyrophosphoric acid, boric acid and oxalic acid, at a temperature of between about 0° and about 200°, under a pressure of between about 1 and 300 atmospheres and in an inert solvent, e.g., ether, tetrahydrofuran, dioxane, methylene chloride, benzene, toluene and xylene.

Furthermore, esters of Formula I ($R_1$ is not H) can be produced by reacting a metallic salt of a carboxylic acid of Formula I ($R_1 = $ H), preferably the alkali metal, lead, or silver salt, with an alkyl halogenide, e.g., those of the formula R₅Cl, optionally in an inert solvent, for example ether, benzene, DMF, or petroleum ether, or with an alkyl chlorosulfite, e.g., those of the formula R₅-OSOCl, and subsequent thermolysis of the thus-obtained adduct.

It is also possible to esterify the alcohols of Formula I (R₂ = [H, OH], R₃ = H; R₂ = [H, OH], R₃ = OH; R₂ = O, R₃ = OH) with ketenes. The reaction is preferably conducted in an inert solvent, e.g., ether, benzene or toluene and in the presence of an acidic catalyst, e.g., sulfuric acid or p-toluenesulfonic acid.

Furthermore, esters of Formula I (R₁ is not H) can be produced by the transesterification of other esters which correspond to Formula I but wherein R₁ is not H, with an excess of the respective alcohol, or by reacting the carboxylic acid of Formula I (R₁ = H) with any desired other ester of the respective alcohol, which is preferably employed in excess. Analogously, esters of Formula I can be obtained by the interesterification of alcohols of Formula I (R₂ = [H, OH], R₃ = H; R₂ = [H, OH], R₃ = OH; R₂ = O, R₃ = OH) with an excess of a lower alkyl ester, or by the transesterification of other esters which correspond to Formula I but wherein R₂ = (H, esterified OH), R₃ = H; R₂ = (H, esterified OH), R₃ = OH; R₂ = (H, esterified OH), R₃ = esterified OH; R₂ = (H, OH), R₃ = esterified OH; or R₂ = O, R₃ = esterified OH, with an excess of the carboxylic acid to be esterified. The reaction is conducted in accordance with the interesterification methods described in the literature, especially in the presence of a basic or acidic catalyst, e.g., sodium ethylate or sulfuric acid, at a temperature of between about 0° and the boiling temperature. Preferably, the process is conducted so that, after the equilibrium has been attained, one reactant is eliminated from the equilibrium mixture by distillation.

The compounds of Formula I generally have several centers of asymmetry and in all cases at least two. Therefore, they are for the most part obtained as mixtures of various stereoisomeric forms, e.g., as a racemate or usually as a mixture of racemates. Since different racemates are diastereomeric with respect to one another, they can be isolated from their mixtures due to their differing physical properties, and thus can be obtained in the pure form, for example by recrystallization from suitable solvents (wherein it is possible to employ especially, instead of the compounds proper, well-crystallizing derivatives), by distillative separation, but particularly with the aid of chromatographic methods, wherein it is possible to utilize adsorption chromatography or distribution chromatography, as well as mixed modes of operation.

The racemates can be separated into the optical antipodes thereof in accordance with any of a large number of conventional methods as disclosed in the literature. Chemical methods of separation are preferred. According to this method, diastereomers are formed from the racemic mixture by reaction with an optically active auxiliary agent. Thus, it is optionally possible to react an optically active base with the carboxyl group of a compound of Formula I (R₁ = H). For example, diastereomeric salts of the compounds of Formula I can be formed with optically active amines, such as quinine, cinchonidine, brucine, cinchonine, hydroxyhydrindamine, morphine, 1-phenylethylamine, 1-naphthylethylamine, phenyloxynaphthylmethylamine, quinidine, strychnine, basic amino acids, such as lysine, arginine, or the amino acid esters. In a similar manner, ester diastereomers can be obtained by the esterification of compounds of Formula I (R₁ = H) with optically active alcohols, e.g., borneol, menthol, 2-octanol. The difference in the solubility of the thus-produced diastereomeric salts and/or esters makes it possible to effect the selective crystallization of one form and the regeneration of the respective optically active compounds from the mixture.

The hydroxy acids and hydroxy esters of Formula I (R₂ = [H,OH], R₃ = H; R₂ = [H,OH], R₃ = OH; R₂ = O, R₃ = OH) can furthermore be converted into suitable diastereomeric esters by esterification with an optically active acid, e.g., (+)- and (−)- tartaric acid, dibenzoyl-(+)- and -(−)-tartaric acid, diacetyl-(+)- and -(−)-tartaric acid, camphoric acid, β-camphorsulfonic acid, (+)- and (−)-mandelic acid, (+)- and (−)-malic acid, (+)- and (−)-2-phenylbutyric acid, (+)-dinitrodiphenic acid or (+)- and (−)-lactic acid. These esters can be separated on the basis of their differing solubilities into respective isomers. The optically active compounds of Formula I are then obtained in each case by the saponification of the pure diastereomer. It is also possible to produce first of all the acidic phthalic acid or succinic acid esters with phthalic acid anhydride or succinic acid anhydride, and then to convert the thus-obtained dibasic acids and/or the monoesters thereof with one of the above-mentioned, optically active bases into the diastereomeric salts, and then to produce the pure enantiomers therefrom. By reaction with optically active ketone reagents, menthyl hydrazine or menthyl semicarbazide, the corresponding diastereomeric hydrazones and/or semicarbazones can be produced from the keto acids and the keto esters of Formula I (R₂ = O). Form these products, the pure enantiomers can likewise be obtained. Especially advantageous is the separation of the racemates or racemate mixtures by chromatography. It is possible to employ either optically active substrate materials, e.g., tartaric acid, amylose, cane sugar, cellulose or acetyl cellulose, and optically inactive and/or optically active eluents for the separation into the pure enantiomers, or an optically inactive substrate can be used, e.g., silica gel or aluminum oxide, in combination with an optically active mobile phase. The optical antipodes can also be separated biochemically by a selective enzymatic reaction. Thus, the racemic acids of Formula I (R₁ = H) can be subjected to an oxidase or optionally a decarboxylase, which destroys one form by oxidation or decarboxylation while the other form remains unaffected. It is furthermore possible to employ a hydrolase in case of a functional acid derivative of the racemic mixture for the preferred formation of an optically active form. Thus, esters or amides of the acids of Formula I (R₁ = H) can be exposed to the effect of a hydrolase, which selectively saponifies one enantiomer and leaves the other one unchanged.

Furthermore, it is of course possible to obtain optically active compounds in accordance with the described methods by the use of starting materials which already are optically active.

If the compounds are produced by reacting a compound of Formula II wherein D is

with a compound of Formula II wherein W is H, then the residues $-A-COOR_1$ and $-S-R_4$ are normally in the trans-position, i.e., when the alkylthio group is in the β-position, the omega-carboxy- or carbalkoxyalkyl group is in the α-position, and vice versa.

If a compound of Formula I is converted into another compound of Formula I, or a precursor with certain steric characteristics on one or more carbon atoms is converted into a compound of Formula I, with the formation of a new center of asymmetry, it is possible to effect, by controlling the reaction in a certain way, that this carbon atom has predominantly a specific and preferably the desired, configuration.

For example, in the addition of a compound of Formula III where W is H to a compound of Formula II wherein D is

and $R_3$ is α-acyloxy of up to 4 carbon atoms, the alkylthio group enters predominantly in the β-position. The corresponding 4β-hydroxy-2-(omega-carboxyalkyl)-3β-alkylthiocyclopentanone is obtained, for example, from 4α-bromo-2-(omega-carboxyalkyl)-2-cyclopentenes by the addition of a compound of Formula II wherein W is H and subsequent hydrolysis with configuration reversal in the 4-position.

Compounds of Formula I wherein $R_1$ is H can be converted into one of the physiologically acceptable metal or ammonium salts thereof by treatment with a base. Expecially suitable as salts are the sodium, potassium, magnesium, calcium and ammonium salts, including substituted ammonium salts, e.g., dimethyl- and diethylammonium, monoethanol-, diethanol- and triethanolammonium, cyclohexylammonium, dicyclohexylammonium and dibenzylethylenediammonium salts.

Conversely, compounds of Formula I can be liberated from the metal and ammonium salts thereof by treatment with an acid, especially a mineral acid, e.g., hydrochloric and sulfuric acid.

The novel compounds can be utilized in a mixture with solid, liquid and/or semiliquid excipients as drugs in human or veterinary medicine. Suitable vehicles are those organic or inorganic materials amenable to parenteral, enteral or topical application and which do not react with the novel compounds, e.g., water, vegetable oils, benzyl alcohols, polyethylene glycols, gelatin, lactose, amylose, magnesium stearate, talc, vaseline, cholesterol. Especially suitable for parenteral application are solutions, preferably oily or aqueous solutions, as well as suspensions, emulsions or implants. Feasible for enteral administration are tablets, dragees, syrups, elixirs, or suppositories, and for topical application ointments, creams or powders. The aforementioned preparation can optionally be sterilized or mixed with auxiliary agents, such as lubricants, preservatives, stabilizers, or wetting agents, emulsifiers, salts for influencing the osmotic pressure, buffers, coloring, flavoring and/or aromatous substances and/or other effective agents, e.g., vitamins.

The substances are preferably administered in a dosage of 0.1 – 2,000 mg. per dosage unit.

Pharmaceutical preparations containing natural prostaglandines are known e.g., from the German Offenlegungsschriften 1 692 035, 1 939 331, 1 943 492 and 1 954 046. The pharmaceutical formulations described in these applications are appropriate for pharmaceutical preparations containing compounds of Formula I.

The IR spectra set forth hereinbelow were recorded with Perkin Elmer 6 as the film, and the NMR spectra were measured with Varian HA 100 or A 60 in $CDCl_3$ against tetramethylsilane as the internal standard.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. The temperatures herein are in degrees Celsius.

EXAMPLE 1

A mixture of 6 g. of 2-(6-carboxyhexyl)-2-cyclopentenone, 10 ml. of propylthiol, and 7.2 ml. of piperidine is allowed to stand at room temperature for 5 days, then diluted with 150 ml. of ether, the ether phase washed first with a mixture of 60 ml. of ice water and 6 ml. of concentrated HCl and then with saturated aqueous NaCl solution, dried over $Na_2SO_4$, the solvent distilled off, and the residue purified by chromatography (silica gel/$CH_3OH$ : $CHCl_3$ = 1 : 9), thus obtaining 2-(6-carboxyhexyl)-3-propylthiocyclopentanone as an oil; $R_f$ = 0.3 (silica gel/chloroform : methanol = 95 : 5).

| Analysis: | C | H | S |
|---|---|---|---|
| Calculated: | 62.9 % | 9.15 % | 11.19 % |
| Found: | 61.5 % | 9.4 % | 10.95 % |

IR spectrum: bands at 1695, 1730, 2860, and 2940 $cm^{-1}$, broad band between 3000 and 3400 $cm^{-1}$.

NMR spectrum: signals at 0.86 p.p.m., 3.0 p.m.p. and 9.75 p.p.m.

Analogously, using the following starting materials:
hexanethiol
heptanethiol
octanethiol
nonanethiol
2-hydroxyethanethiol
2-hydroxypropanethiol
2-hydroxybutanethiol
2-hydroxyisobutanethiol
2-hydroxypentanethiol
2-hydroxyisopentanethiol
2-hydroxyhexanethiol
2-hydroxyisohexanethiol
2-hydroxyheptanethiol
2-hydroxyisoheptanethiol
2-hydroxyoctanethiol
2-hydroxyisooctanethiol
2-hydroxynonanethiol
2-hydroxyisononanethiol
2-hydroxy-5,5-dimethylhexylthiol
2-hydroxy-6,6-dimethylheptanethiol
2-hydroxy-7,7-dimethyloctanethiol
2-hydroxy-8,8-dimethylnonanethiol 2-hydroxy-2-methylhexanethiol
2-hydroxy-2-methylheptanethiol
2-hydroxy-2-methyloctanethiol
2-hydroxy-2-methylnonanethiol
2-hydroxy-3,3-dimethylhexanethiol
2-hydroxy-3,3-dimethylheptanethiol
2-hydroxy-3,3-dimethyloctanethiol
2-hydroxy-3,3-dimethylnonanethiol
2-hydroxy-2,3,3-trimethylhexanethiol
2-hydroxy-2,3,3-trimethylheptanethiol
2-hydroxy-2,3,3-trimethyloctanethiol
2-hydroxy-2,3,3-trimethylnonanethiol
2-hydroxy-2,5,5-trimethylhexanethiol
2-hydroxy-2,6,6-trimethylheptanethiol
2-hydroxy-2,7,7-trimethyloctanethiol
2-hydroxy-2,8,8-trimethylnonanethiol
2-hydroxy-6,6,6-trifluorohexanethiol
2-hydroxy-7,7,7-trifluoroheptanethiol
2-hydroxy-8,8,8-trifluorooctanethiol
2-hydroxy-9,9,9-trifluorononanethiol
2-hydroxy-2-methyl-6,6,6-trifluorohexanethiol
2-hydroxy-2-methyl-7,7,7-trifluoroheptanethiol
2-hydroxy-2-methyl-8,8,8-trifluorooctanethiol
2-hydroxy-2-methyl-9,9,9-trifluorononanethiol
2-hydroxy-3,3-dimethyl-6,6,6-trifluorohexanethiol
2-hydroxy-3,3-dimethyl-7,7,7-trifluoroheptanethiol
2-hydroxy-3,3-dimethyl-8,8,8-trifluorooctanethiol
2-hydroxy-3,3-dimethyl-9,9,9-trifluorononanethiol
2-hydroxy-2,3,3-trimethyl-6,6,6-trifluorohexanethiol
2-hydroxy-2,3,3-trimethyl-7,7,7-trifluoroheptanethiol
2-hydroxy-2,3,3-trimethyl-8,8,8-trifluorooctanethiol
2-hydroxy-2,3,3-trimethyl-9,9,9-trifluorononanethiol
2-hydroxy-2-phenylethanethiol
2-hydroxy-3-phenylpropanethiol
2-hydroxy-4-phenylbutanethiol
2-hydroxy-5-phenylpentanethiol
2-hydroxy-6-phenylhexanethiol
2-hydroxy-7-phenylheptanethiol
2-hydroxy-2-methyl-2-phenylethanethiol
2-hydroxy-2-methyl-3-phenylpropanethiol
2-hydroxy-2-methyl-4-phenylbutanethiol
2-hydroxy-2-methyl-5-phenylpentanethiol
2-hydroxy-2-methyl-6-phenylhexanethiol
2-hydroxy-2-methyl-7-phenylheptanethiol
2-hydroxy-3,3-dimethyl-3-phenylpropanethiol
2-hydroxy-3,3-dimethyl-4-phenylbutanethiol
2-hydroxy-3,3-dimethyl-5-phenylpentanethiol
2-hydroxy-3,3-dimethyl-6-phenylhexanethiol
2-hydroxy-3,3-dimethyl-7-phenylheptanethiol
2-hydroxy-2,3,3-trimethyl-3-phenylpropanethiol
2-hydroxy-2,3,3-trimethyl-4-phenylbutanethiol
2-hydroxy-2,3,3-trimethyl-5-phenylpentanethiol
2-hydroxy-2,3,3-trimethyl-6-phenylhexanethiol
2-hydroxy-2,3,3-trimethyl-7-phenylheptanethiol,
the final products set forth below are obtained by reaction with 2-(6-carboxyhexyl)-2-cyclopentenone:
2-(6-carboxyhexyl)-3-hexylthio-cyclopentanone
2-(6-carboxyhexyl)-3-heptylthio-cyclopentanone
2-(6-carboxyhexyl)-3-octylthio-cyclopentanone
2-(6-carboxyhexyl)-3-nonylthio-cyclopentanone
2-(6-carboxyhexyl)-3-(2-hydroxyethylthio)-cyclopentanone
2-(6-carboxyhexyl)-3-(2-hydroxypropylthio)-cyclopentanone
2-(6-carboxyhexyl)-3-(2-hydroxybutylthio-cyclopentanone
2-(6-carboxyhexyl)-3-(2-hydroxyisobutylthio)-cyclopentanone
2-(6-carboxyhexyl)-3-(2-hydroxypentylthio)-cyclopentanone
2-(6-carboxyhexyl)-3-(2-hydroxyisopentylthio)-cyclopentanone
2-(6-carboxyhexyl)-3-(2-hydroxyhexylthio)-cyclopentanone
2-(6-carboxyhexyl)-3-(2-hydroxyisohexylthio)-cyclopentanone
2-(6-carboxyhexyl)-3-(2-hydroxyheptylthio)-cyclopentanone
2-(6-carboxyhexyl)-3-(2-hydroxyisoheptylthio)-cyclopentanone
2-(6-carboxyhexyl)-3-(2-hydroxyoctylthio)-cyclopentanone
2-(6-carboxyhexyl)-3-(2-hydroxyisooctylthio)-cyclopentanone
2-(6-carboxyhexyl)-3-(2-hydroxynonylthio)-cyclopentanone
2-(6-carboxyhexyl)-3-(2-hydroxyisononylthio)-cyclopentanone
2-(6-carboxyhexyl)-3-(2-hydroxy-5,5-dimethylhexylthio)-cyclopentanone
2-(6-carboxyhexyl)-3-(2-hydroxy-6,6-dimethylheptylthio)-cyclopentanone
2-(6-carboxyhexyl)-3-(2-hydroxy-7,7-dimethyloctylthio)-cyclopentanone
2-(6-carboxyhexyl)-3-(2-hydroxy-8,8-dimethylnonylthio)-cyclopentanone
2-(6-carboxyhexyl)-3-(2-hydroxy-2-methylhexylthio)-cyclopentanone
2-(6-carboxyhexyl)-3-(2-hydroxy-2-methylheptylthio)-cyclopentanone
2-(6-carboxyhexyl)-3-(2-hydroxy-2-methyloctylthio)-cyclopentanone
2-(6-carboxyhexyl)-3-(2-hydroxy-2-methylnonylthio)-cyclopentanone
2-(6-carboxyhexyl)-3-(2-hydroxy-3,3-dimethylhexylthio)-cyclopentanone
2-(6-carboxyhexyl)-3-(2-hydroxy-3,3-dimethylheptylthio)-cyclopentanone
2-(6-carboxyhexyl)-3-(2-hydroxy-3,3-dimethyloctylthio)-cyclopentanone
2-(6-carboxyhexyl)-3-(2-hydroxy-3,3-dimethylnonylthio)-cyclopentanone
2-(6-carboxyhexyl)-3-(2-hydroxy-2,3,3-trimethylhexylthio)-cyclopentanone
2-(6-carboxyhexyl)-3-(2-hydroxy-2,3,3-trimethylheptylthio)-cyclopentanone
2-(6-carboxyhexyl)-3-(2-hydroxy-2,3,3-trimethyloctylthio)-cyclopentanone
2-(6-carboxyhexyl)-3-(2-hydroxy-2,3,3-trimethylnonylthio)-cyclopentanone
2-(6-carboxyhexyl)-3-(2-hydroxy-2,5,5-trimethylhexylthio)-cyclopentanone
2-(6-carboxyhexyl)-3-(2-hydroxy-2,6,6-trimethylheptylthio)-cyclopentanone
2-(6-carboxyhexyl)-3-(2-hydroxy-2,7,7-trimethyloctylthiol)-cyclopentanone
2-(6-carboxyhexyl)-3-(2-hydroxy-2,8,8-trimethylnonylthio)-cyclopentanone
2-(6-carboxyhexyl)-3-(2-hydroxy-6,6,6-trifluorohexylthio)-cyclopentanone 2-(6-carboxyhexyl)-3-(2-hydroxy-7,7,7-trifluoroheptylthio)-cyclopentanone
2-(6-carboxyhexyl)-3-(2-hydroxy-8,8,8-trifluorooctylthio)-cyclopentanone
2-(6-carboxyhexyl)-3-(2-hydroxy-9,9,9-trifluorononylthio)-cyclopentanone
2-(6-carboxyhexyl)-3-(2-hydroxy-2-methyl-6,6,6-trifluorohexylthio)-cyclopentanone
2-(6-carboxyhexyl)-3-(2-hydroxy-2-methyl-7,7,7-trifluoroheptylthio)-cyclopentanone
2-(6-carboxyhexyl)-3-(2-hydroxy-2-methyl-8,8,8-trifluorooctylthio)-cyclopentanone
2-(6-carboxyhexyl)-3-(2-hydroxy-2-methyl-9,9,9-trifluorononylthio)-cyclopentanone
2-(6-carboxyhexyl-3-(2-hydroxy-3,3-dimethyl-6,6,6-trifluorohexylthio)-cyclopentanone
2-(6-carboxyhexyl)-3-(2-hydroxy-3,3-dimethyl-7,7,7-trifluoroheptylthio)-cyclopentanone
2-(6-carboxyhexyl)-3-(2-hydroxy-3,3-dimethyl-8,8,8-trifluorooctylthio)-cyclopentanone
2-(6-carboxyhexyl)-3-(2-hydroxy-3,3-dimethyl-9,9,9-trifluorononylthio)-cyclopentanone
2-(6-carboxyhexyl)-3-(2-hydroxy-2,3,3-trimethyl-6,6,6-trifluorohexylthio)-cyclopentanone
2-(6-carboxyhexyl)-3-(2-hydroxy-2,3,3-trimethyl-7,7,7-trifluoroheptylthio)-cyclopentanone
2-(6-carboxyhexyl)-3-(2-hydroxy-2,3,3-trimethyl-8,8,8-trifluorooctylthio)-cyclopentanone
2-(6-carboxyhexyl)-3-(2-hydroxy-2,3,3-trimethyl-9,9,9-trifluorononylthio)-cyclopentanone
2-(6-carboxyhexyl)-3-(2-hydroxy-2-phenylethylthio)-cyclopentanone
2-(6-carboxyhexyl)-3-(2-hydroxy-3-phenylpropylthio)-cyclopentanone
2-(6-carboxyhexyl)-3-(2-hydroxy-4-phenylbutylthio)-cyclopentanone
2-(6-carboxyhexyl)-3-(2-hydroxy-5-phenylpentylthio)-cyclopentanone
2-(6-carboxyhexyl)-3-(2-hydroxy-6-phenylhexylthio)-cyclopentanone
2-(6-carboxyhexyl)-3-(2-hydroxy-7-phenylheptylthio)-cyclopentanone
2-(6-carboxyhexyl)-3-(2-hydroxy-2-methyl-2-phenylethylthio)-cyclopentanone
2-(6-carboxyhexyl)-3-(2-hydroxy-2-methyl-3-phenylpropylthio)-cyclopentanone
2-(6-carboxyhexyl)-3-(2-hydroxy-2methyl-4-phenylbutylthio)-cyclopentanone
2-(6-carboxyhexyl)-3-(2-hydroxy-2-methyl-5-phenylpentylthio)-cyclopentanone
2(6-carboxyhexyl)-3-(2-hydroxy-2-methyl-6-phenylhexylthio-cyclopentanone
2-(6-carboxyhexyl)-3-(2-hydroxy-2-methyl-7-phenylheptylthio-cyclopentanone
2-(6-carboxyhexyl)-3-(2-hydroxy-3,3-dimethyl-3-phenylpropylthio)-cyclopentanone
2-(6-carboxyhexyl)-3-(2-hydroxy-3,3-dimethyl-4-phenylbutylthio)-cyclopentanone
2-(6-carboxyhexyl)-3-(2-hydroxy-3,3-dimethyl-5-phenylpentylthio)-cyclopentanone
2-(6-carboxyhexyl)-3-(2-hydroxy-3,3-dimethyl-6-phenylhexylthio)-cyclopentanone
2-(6-carboxyhexyl)-3-(2-hydroxy-3,3-dimethyl-7-phenylheptylthio-cyclopentanone
2-(6-carboxyhexyl)-3-(2-hydroxy-2,3,3-trimethyl-3-phenylpropylthio)-cyclopentanone
2-(6-carboxyhexyl)-3-(2-hydroxy-2,3,3-trimethyl-4-phenylbutylthio)-cyclopentanone
2-(6carboxyhexyl)-3-(2-hydroxy-2,3,3-trimethyl-5-phenylpentylthio)-cyclopentanone
2-(6-carboxyhexyl)-3-(2-hydroxy-2,3,3-trimethyl-6-phenylhexylthio)-cyclopentanone
2-(6-carboxyhexyl)-3-(2-hydroxy-2,3,3-trimethyl-7-phenylheptylthio)-cyclopentanone.

EXAMPLE 2

5 g. of dry triethylamine is added to a mixture of 3.1 g. of 2-(6-carboxyhexyl)-2-cyclopentenone and 1.5 g. of 2-hydroxyheptanethiol dissolved in 30 ml. of dry ethanol; the reaction mixture is refluxed for 8 hours and then introduced into a mixture of 150 ml. of ice water and 10 ml. of concentrated HCl, extracted with 200 ml. of ether, and the organic phase is washed with saturated aqueous NaCl solution, dried over $Na_2SO_4$, the solvent is evaporated, and the product, obtained after purifying the residue by chromatography (silica gel/$CH_3OH$ : $CHCl_3$ = 1 : 9), is 2-(6-carboxyhexyl)-3-(2-hydroxyheptylthio)-cyclopentanone as an oil. $R_f$ = 0.2 (silica gel/chloroform : methanol = 95 : 5).

| Analysis: | C | H | S |
|---|---|---|---|
| Calculated: | 63.65 % | 9.56 % | 8.94 % |
| Found: | 62.7 % | 9.5 % | 8.3 % |

IR spectrum: bands at 1700, 1730, 2880, and 2950 $cm^{-1}$, broad band between 3000 and 3500 $cm^{-1}$.

NMR spectrum: signals at 0.9 p.p.m., 3.1 p.p.m., 3.75 p.p.m., and 6.8 p.p.m.

Analogously, with the use of the following starting compounds:
heptanethiol
nonanethiol
2-hydroxyheptanethiol
2-hydroxynonanethiol
2-hydroxy-2-methylheptanethiol
2-hydroxy-2-methylnonanethiol
2-hydroxy-3,3-dimethylheptanethiol
2-hydroxy-3,3-dimethylnonanethiol
2-hydroxy-6,6,-dimethylheptanethiol
2-hydroxy-8,8-dimethylnonanethiol
2-hydroxy-2,3,3-trimethylheptanethiol
2-hydroxy-2,3,3-trimethylnonanethiol
2-hydroxy-2,6,6-trimethylheptanethiol
2-hydroxy-2,8,8-trimethylnonanethiol
2-hydroxy-7,7,7-trifluoroheptanethiol
2-hydroxy-9,9,9-trifluorononanethiol
2-hydroxy-2-methyl-7,7,7-trifluoroheptanethiol
2-hydroxy-2-methyl-9,9,9-trifluorononanethiol
2-hydroxy-3,3-dimethyl-7,7,7-trifluoroheptanethiol
2-hydroxy-3,3-dimethyl-9,9,9-trifluorononanethiol
2-hydroxy-2,3,3-trimethyl-7,7,7-trifluoroheptanethiol
2-hydroxy-2,3,3-trimethyl-9,9,9-trifluorononanethiol
2-hydroxy-3-phenylpropanethiol
2-hydroxy-5-phenylpentanethiol
2-hydroxy-2-methyl-3-phenylpropanethiol
2-hydroxy-2-methyl-5-phenylpentanethiol
2-hydroxy-3,3-dimethyl-3-phenylpropanethiol
2-hydroxy-3,3-dimethyl-5-phenylpentanethiol
2-hydroxy-2,3,3-trimethyl-3-phenylpropanethiol 2-hydroxy-2,3,3-trimethyl-5-phenylpentanethiol,
the final products set forth below are obtained by reaction with 2-(6-carbethoxyhexyl)-2-cyclopentenone:

2-(6-carbethoxyhexyl)-3-heptylthio-cyclopentanone
2-(6-carbethoxyhexyl)-3-nonylthio-cyclopentanone
2-(6-carbethoxyhexyl)-3-(2-hydroxyheptylthio)-cyclopentanone
2-(6-carbethoxyhexyl)-3-(2-hydroxynonylthio)-cyclopentanone
2-(6-carbethoxyhexyl)-3-(2-hydroxy-2-methylheptylthio)-cyclopentanone
2-(6-carbethoxyhexyl)-3-(2-hydroxy-2-methylnonylthio)-cyclopentanone
2-(6-carbethoxyhexyl)-3-(2-hydroxy-3,3-dimethylheptylthio-cyclopentanone
2-(6-carbethoxyhexyl)-3-(2-hydroxy-3,3-dimethylnonylthio)-cyclopentanone
2-(6-carbethoxyhexyl)-3-(2-hydroxy-6,6-dimethylheptylthio-cyclopentanone
2-(6-carbethoxyhexyl)-3-(2-hydroxy-8,8-dimethylnonylthio)-cyclopentanone
2-(6-carbethoxyhexyl)-3-(2-hydroxy-2,3,3-trimethylheptylthio)-cyclopentanone
2-(6-carbethoxyhexyl)-3-(2-hydroxy-2,3,3-trimethylnonylthio)-cyclopentanone
2-(6-carbethoxyhexyl)-3-(2-hydroxy-2,6,6-trimethylheptylthio)-cyclopentanone
2-(6-carbethoxyhexyl)-3-(2-hydroxy-2,8,8-trimethylnonylthio)-cyclopentanone
2-(6-carbethoxyhexyl)-3-(2-hydroxy-7,7,7-trifluoroheptylthio)-cyclopentanone
2-(6-carbethoxyhexyl)-3-(2-hydroxy-9,9,9-trifluorononylthio)-cyclopentanone
2-(6-carbethoxyhexyl)-3-(2-hydroxy-2-methyl-7,7,7-trifluoroheptylthio)-cyclopentanone
2-(6-carbethoxyhexyl)-3-(2-hydroxy-2-methyl-9,9,9-trifluorononylthio)-cyclopentanone
2-(6-carbethoxyhexyl)-3-(2-hydroxy-3,3-dimethyl-7,7,7-trifluoroheptylthio)-cyclopentanone
2-(6-carbethoxyhexyl)-3-(2-hydroxy-3,3-dimethyl-9,9,9-trifluorononylthio)-cyclopentanone
2-(6-carbethoxyhexyl)-3-(2-hydroxy-2,3,3-trimethyl-7,7,7-trifluoroheptylthio)-cyclopentanone
2-(6-carbethoxyhexyl)-3-(2-hydroxy-2,3,3-trimethyl-9,9,9-trifluorononylthio)-cyclopentanone
2-(6-carbethoxyhexyl)-3-(2-hydroxy-3-phenylpropylthio)-cyclopentanone
2(6-carbethoxyhexyl)-3-(2-hydroxy-5-phenylpentylthio)-cyclopentanone
2-(6-carbethoxyhexyl)-3-(2-hydroxy-2-methyl-3-phenylpropylthio)-cyclopentanone
2-(6-carbethoxyhexyl)-3-(2-hydroxy-2-methyl-5-phenylpentylthio)-cyclopentanone
2-(6-carbethoxyhexyl)-3-(2-hydroxy-3,3-dimethyl-3-phenylpropylthio)-cyclopentanone
2-(6-carbethoxyhexyl)-3-(2-hydroxy-3,3-dimethyl-5-phenylpentylthio)-cyclopentanone
2-(6-carbethoxyhexyl)-3-(2-hydroxy-2,3,3-trimethyl-3-phenylpropylthio)-cyclopentanone
2-(6-carbethoxyhexyl)-3-(2-hydroxy-2,3,3-trimethyl-5-phenylpentylthio)-cyclopentanone.

EXAMPLE 3

3.2 g. of 2-(6-carbethoxyhexyl)-2-cyclopentenone, dissolved in 20 ml. of dry ethanol, is added to a solution of sodium heptanethiolate (producible by dissolving 0.24 g. of sodium in 30 ml. of dry ethanol and adding 1.3 g. of heptylthiol); the reaction mixture is agitated under nitrogen for 24 hours at 40°, then diluted with 150 ml. of ice water and 10 ml. of concentrated HCl, extracted with $CH_2Cl_2$, washed with saturated aqueous NaCl solution, dried over $Na_2SO_4$, and the solvent is distilled off. After purifying the residue by chromatography, 2-(6-carbethoxyhexyl)-3-heptylthio-cyclopentanone is obtained. $R_f = 0.7$ (silica gel/chloroform).

| Analysis: | C | H | S |
|---|---|---|---|
| Calculated: | 68.07 % | 10.33 % | 8.65 % |
| Found: | 67.8 % | 10.4 % | 8.6 % |

IR spectrum: bands at 1730, 2870, and 2950 $cm^{-1}$.
NMR spectrum: signals at 0.9 p.p.m. and 3.0 p.p.m.; signal between 3.95 p.p.m. and 4.3 p.p.m. (quartet).

Analogously, with the use of the following starting compounds:
sodium 2-hydroxy-2-p-tolylethanethiolate
sodium 2-hydroxy-3-p-tolylpropanethiolate
sodium 2-hydroxy-4-p-tolylbutanethiolate
sodium 2-hydroxy-5-p-tolylpentanethiolate
sodium 2-hydroxy-2-methyl-2-p-tolylethanethiolate
sodium 2-hydroxy-2-methyl-3-n-tolylpropanethiolate
sodium 2-hydroxy-2-methyl-4-p-tolylbutanethiolate
sodium 2-hydroxy-2-methyl-5-p-tolylpentanethiolate
sodium 2-hydroxy-3,3-dimethyl-3-p-tolylpropanethiolate
sodium 2-hydroxy-3,3-dimethyl-4-p-tolylbutanethiolate
sodium 2-hydroxy-3,3-dimethyl-5-p-tolylpentanethiolate
sodium 2-hydroxy-2,3,3-trimethyl-3-p-tolylpropanethiolate
sodium 2-hydroxy-2,3,3-trimethyl-4-p-tolylbutanethiolate
sodium 2-hydroxy-2,3,3-trimethyl-5-p-tolylpentanethiolate,
the products set forth below are obtained by reaction with 2-(6-carbethoxyheptyl)-2-cyclopentenone
2-(6-carbethoxyhexyl)-3-(2-hydroxy-2-p-tolylethylthio)-cyclopentanone
2-(6-carbethoxyhexyl)-3-(2-hydroxy-3-p-tolylpropylthio)-cyclopentanone
2-(6-carbethoxyhexyl)-3-(2-hydroxy-4-p-tolylbutylthio)-cyclopentanone
2-(6-carbethoxyhexyl)-3-(2-hydroxy-5-p-tolylpentylthio)-cyclopentanone
2-(6-carbethoxyhexyl)-3-(2-hydroxy-2-methyl-2-p-tolylethylthio)-cyclopentanone
2-(6-carbethoxyhexyl)-3-(2-hydroxy-2-methyl-3-p-tolylpropylthio)-cyclopentanone
2-(6-carbethoxyhexyl)-3-(2-hydroxy-2-methyl-4-p-tolylbutylthio)-cyclopentanone
2-(6-carbethoxyhexyl)-3-(2-hydroxy-2-methyl-5-p-tolylpentylthio)-cyclopentanone
2-(6-carbethoxyhexyl)-3-(2-hydroxy-3,3-dimethyl-3-p-tolylpropylthio)-cyclopentanone
2-(6-carbethoxyhexyl)-3-(2-hydroxy-3,3-dimethyl-4-p-tolylbutylthio)-cyclopentanone
2-(6-carbethoxyhexyl)-3-(2-hydroxy-3,3-dimethyl-5- p-tolylpentylthio)-cyclopentanone
2-(6carbethoxyhexyl)-3-(2-hydroxy-2,3,3-trimethyl-3-p-tolylpropylthio)-cyclopentanone
2-(6-carbethoxyhexyl)-3-(2-hydroxy-2,3,3-trimethyl-4-p-tolylbutylthio)-cyclopentanone
2-(6-carbethoxyhexyl)-3-(2-hydroxy-2,3,3-trimethyl-5-p-tolylpentylthio)-cyclopentanone.

EXAMPLE 4

Analogously to Example 1, with the use of the following starting materials:
2-(4-carbethoxybutyl)-2-cyclopentenone
2-(5-carbethoxypentyl)-2-cyclopentenone
2-(7-carbethoxyheptyl)-2-cyclopentenone
2-(8-carbethoxyoctyl)-2-cyclopentenone,
the final products set forth below are obtained by reaction with 2-hydroxyheptanethiol:
2-(4-carbethoxybutyl)-3-(2-hydroxyheptylthio)-cyclopentanone
2-(5-carbethoxypentyl)-3-(2-hydroxyheptylthio)-cyclopentanone
2-(7-carbethoxyheptyl)-3-(2-hydroxyheptylthio)-cyclopentanone
2-(8-carbethoxyoctyl)-3-(2-hydroxyheptylthio)-cyclopentanone;
by reaction with 2-hydroxynonanethiol:
2-(4-carbethoxybutyl)-3-(2-hydroxynonylthio)-cyclopentanone
2-(5-carbethoxypentyl)-3-(2-hydroxynonylthio)-cyclopentanone
2-(7-carbethoxyheptyl)-3-(2-hydroxynonylthio)-cyclopentanone
2-(8-carbethoxyoctyl)-3-(2-hydroxynonylthio)-cyclopentanone;
by reaction with 2-hydroxy-3,3-dimethylheptanethiol:
2-(4-carbethoxybutyl)-3-(2-hydroxy-3,3-dimethylheptylthio)-cyclopentanone
2-(5-carbethoxypentyl)-3-(2-hydroxy-3,3-dimethylheptylthio)-cyclopentanone
2-(7-carbethoxyheptyl)-3-(2-hydroxy-3,3-dimethylheptylthio)-cyclopentanone
2-(8-carbethoxyoctyl)-3-(2-hydroxy-3,3-dimethylheptylthio)-cyclopentanone;
by reaction with 2-hydroxy-3,3-dimethylnonanethiol:
2-(4-carbethoxybutyl)-3-(2-hydroxy-3,3-dimethylnonylthio)-cyclopentanone
2-(5-carbethoxypentyl)-3-(2-hydroxy-3,3-dimethylnonylthio)-cyclopentanone
2-(7-carbethoxyheptyl)-3-(2-hydroxy-3,3-dimethylnonylthio)-cyclopentanone
2-(8-carbethoxyoctyl)-3-(2-hydroxy-3,3-dimethylnonylthio)-cyclopentanone.

EXAMPLE 5

A mixture of 6 g. of 2-(6-carbethoxyhexyl)-2-cyclopentenone, 10 ml. of propanethiol, and 7.2 ml. of piperidine is allowed to stand for 5 days at room temperature, then diluted with 150 ml. of ether, and the ether phase is washed first with a mixture of 60 ml. of ice water and 6 ml. of concentrated HCl, and then with saturated aqueous NaCl solution, dried over NaSO$_4$, and the solvent distilled off. After purifying the residue by chromatography (silica gel/chloroform), 2-(carbethoxyhexyl)-3-propylthio-cyclopentanone is produced as an oil.

$R_f$ = 0.7 (silica gel/chloroform).

| Analysis:   | C       | H      | S      |
|-------------|---------|--------|--------|
| Calculated: | 64.93 % | 9.61 % | 10.2 % |
| Found:      | 65.6 %  | 9.7 %  | 9.8 %  |

IR spectrum: bands at 1730, 2870, and 2950 cm$^{-1}$.
NMR spectrum: signals at 1.0 p.p.m., 3.0 p.p.m., and 4.0 – 4.22 p.p.m. (quartet).

EXAMPLE 6

3.2 g. of 2-(6-cyanohexyl)-3-heptylthio-cyclopentanone (obtainable from the potassium salt of the ethyl ester of 2-oxocyclopentanecarboxylic acid and 6-cyanohexyl bromide, treating the thus-obtained ethyl ester of 1-(6-cyanohexyl)-2-oxocyclopentanecarboxylic acid with bromine and subsequently with sulfuric acid, and addition of heptylthiol to the thus-produced 2-(6-cyanohexyl)-2-cyclopentenone) is refluxed for 3 hours in a mixture of 30 ml. of water and 20 ml. of concentrated sulfuric acid. After the mixture has been cooled, it is poured into 100 ml. of ice water, extracted twice with respectively 40 ml. of CH$_2$Cl$_2$, the organic phase washed with water, dried over Na$_2$SO$_4$, and the solvent distilled off. After purifying the residue by chromatography (silica gel/chloroform), the thus-obtained product is 2-(6-carboxyhexyl)-3-heptylthio-cyclopentanone.

$R_f$ = 0.3 (silica gel/chloroform: methanol = 95 : 5).

| Analysis:   | C       | H       | S      |
|-------------|---------|---------|--------|
| Calculated: | 66.62 % | 10.01 % | 9.36 % |
| Found:      | 65.5 %  | 9.17 %  | 9.8 %  |

IR spectrum: bands at 1700, 1730, 2860, and 2940 cm$^{-1}$; broad band between 3000 and 3400 cm$^{-1}$.

NMR spectrum: signals at 0.86 p.p.m., 3.0 p.p.m., and 9.75 p.p.m.

EXAMPLE 7

3.4 g. of 2-(6-carboxamidohexyl)-3-heptylthio-cyclopentanone (obtainable from the potassium salt of the ethyl ester of 2-oxocyclopentanecarboxylic acid and 6-carboxamidohexyl bromide [obtainable from 7-bromoheptanoic acid and thionyl chloride and reaction of the thus-produced 7-bromoheptanoic acid chloride with aqueous ammonia], treating the thus-obtained ethyl ester of 1-(6-carboxamidohexyl)-2-oxocyclopentanecarboxylic acid with bromine and subsequently with H$_2$SO$_4$, and addition of heptylthiol to the thus-produced 2-(6-carboxamidohexyl)-2-cyclopentanone) is refluxed for one hour with a mixture of 30 ml. of 2N aqueous NaOH and 10 ml. of ethanol; after cooling, the reaction mixture is poured into 50 ml. of aqueous 2N HCl, twice extracted with respectively 30 ml. of CH$_2$Cl$_2$, and the organic phase is washed with water, dried over $Na_2SO_4$, and the solvent distilled off. After purifying the residue by chromatography (silica gel/chloroform), the product is 2-(6-carboxyhexyl)-3-heptylthio-cyclopentanone.

$R_f = 0.3$ (silica gel/chloroform: methanol = 95 : 5).

| Analysis: | C | H | S |
|---|---|---|---|
| Calculated: | 66.62 % | 10.01 % | 9.36 % |
| Found: | 65.5 % | 9.71 % | 9.8 % |

IR spectrum: bands at 1700, 1730, 2860, and 2940 cm$^{-1}$; broad band between 3000 and 3400 cm$^{-1}$.

NMR spectrum: signals at 0.86 p.p.m., 3.0 p.p.m., and 9.75 p.p.m.

EXAMPLE 8

5.1 g. of 1,1-dibromo-2-(6-carbethoxyhexyl)-3-heptylthio-cyclopentane (obtainable from 2-(6-carboxyhexyl)-3-heptylthio-cyclopentanone by reaction with $PBr_5$ and ethanolysis of the thus-obtained 2-(6-bromocarbonylhexyl)-3-heptylthio-1,1-dibromopentane) is agitated for 4 hours in 100 ml. of a mixture of 1 g. of KOH, 50 ml. of $H_2O$, and 50 ml. of dioxane; after cooling the reaction mixture is poured into 100 ml. of 2N aqueous HCl, extracted twice with respectively 50 ml. of $CH_2Cl_2$, and the organic phase is washed with water and dried over $Na_2SO_4$. The solvent is then distilled off and, after purifying the residue by chromatography (silica gel/chloroform), 2-(6-carboxyhexyl)-3-heptylthio-cyclopentanone is obtained.

$R_f = 0.3$ (silica gel/chloroform: methanol = 95 : 5).

| Analysis: | C | H | S |
|---|---|---|---|
| Calculated: | 66.62 % | 10.01 % | 9.36 % |
| Found: | 65.5 % | 9.71 % | 9.8 % |

IR spectrum: bands at 1700, 1730, 2860, and 2940 cm$^{-1}$; broad band between 3000 and 3400 cm$^{-1}$.

NMR spectrum: signals at 0.86 p.p.m., 3.0 p.p.m., and 9.75 p.p.m.

EXAMPLE 9

5.0 g. of 1α-p-toluenesulfonyloxy-2-(6-carboxyhexyl)-3-heptylthio-cyclopentane (obtainable from 2-(6-carboxyhexyl)-3-heptylthio-cyclopentanol-(1α) and p-toluenesulfonic acid chloride) is refluxed for 2 hours in 60 ml. of 2N aqueous NaOH; after cooling, the reaction mixture is poured into 100 ml. of 2N aqueous HCl, extracted twice with respectively 50 ml. of $CH_2Cl_2$, and the organic phase is washed with water, dried over $Na_2SO_4$, and then the solvent is distilled off. After purifying the residue by chromatography (silica gel/chloroform), the product thus obtained is 2-(6-carboxyhexyl)-3-heptylthio-cyclopentanol-(1β).

$R_f = 0.3$ (silica gel/chloroform: methanol = 95 : 5).

| Analysis: | C | H | S |
|---|---|---|---|
| Calculated: | 66.62 % | 10.01 % | 9.36 % |
| Found: | 65.5 % | 9.71 % | 9.8 % |

IR spectrum: bands at 1700, 1730, 2860, and 2940 cm$^{-1}$; broad band between 3000 and 3400 cm$^{-1}$.

NMR spectrum: signals at 0.86 p.p.m., 3.0 p.p.m., and 9.75 p.p.m.

EXAMPLE 10

2.0 g. of $NaBH_4$ is added to 3.4 g. of 2-(6-carboxyhexyl)-3-heptylthio-cyclopentanone, dissolved in 30 ml. of methanol; the mixture is agitated for 2 hours at 20° and, after cooling, is poured into 100 ml. of saturated aqueous NaCl solution. The mixture is extracted three times with respectively 30 ml. of ether, the organic phase is washed with water, dried over $Na_2SO_4$, and the solvent is distilled off, thus obtaining after purifying the residue by chromatography (silica gel/chloroform), 2-(6-carboxyhexyl)-3-heptylthio-cyclopentanol.

Analogously, by using the following starting compounds:

2-(6-carboxyhexyl)-3-(2-hydroxyheptylthio)-cyclopentanone
2-(6-carboxyhexyl)-3-(2-hydroxynonylthio)-cyclopentanone
2-(6-carboxyhexyl)-3-(2-hydroxy-2-methylheptylthio)-cyclopentanone
2-(6-carboxyhexyl)-3-(2-hydroxy-2-methylnonylthio)-cyclopentanone
2-(6-carboxyhexyl)-3-(2-hydroxy-3,3-dimethylheptylthio)-cyclopentanone
2-(6-carboxyhexyl)-3-(2-hydroxy-3,3-dimethylnonylthio)-cyclopentanone
2-(6-carboxyhexyl)-3-(2-hydroxy-6,6-dimethylheptylthio)-cyclopentanone
2-(6-carboxyhexyl)-3-(2-hydroxy-8,8-dimethylnonylthio)-cyclopentanone
2(6-carboxyhexyl)-3-(2-hydroxy-2,3,3-trimethylheptylthio)-cyclopentanone
2-(6-carboxyhexyl)-3-(2-hydroxy-2,3,3-trimethylnonylthio)-cyclopentanone
2-(6-carboxyhexyl)-3-(2-hydroxy-2,6,6-trimethylheptylthio)-cyclopentanone
2-(6-carboxyhexyl)-3-(2-hydroxy-2,8,8-trimethylnonylthio)-cyclopentanone
2-(6-carboxyhexyl)-3-(2-hydroxy-7,7,7-trifluoroheptylthio)-cyclopentanone
2-(6-carboxyhexyl)-3-(2-hydroxy-9,9,9-trifluorononylthio)-cyclopentanone
2-(6-carboxyhexyl)-3-(2-hydroxy-2-methyl-7,7,7-trifluoroheptylthio)-cyclopentanone
2-(6-carboxyhexyl)-3-(2-hydroxy-2-methyl-9,9,9-trifluorononylthio)-cyclopentanone
2-(6-carboxyhexyl)-3-(2-hydroxy-3,3-dimethyl-7,7,7-trifluoroheptylthio)-cyclopentanone
2-(6-carboxyhexyl)-3-(2-hydroxy-3,3-dimethyl-9,9,9-trifluorononylthio)-cyclopentanone
2-(6-carboxyhexyl)-3-(2-hydroxy-2,3,3-trimethyl-7,7,7-trifluoroheptylthio)-cyclopentanone 2-(6-carboxyhexyl)-3-(2-hydroxy-2,3,3-trimethyl-9,9,9-trifluorononylthio)-cyclopentanone
2-(6-carboxyhexyl)-3-(2-hydroxy-3-phenylpropylthio)-cyclopentanone
2-(6-carboxyhexyl)-3-(2-hydroxy-5-phenylpentylthio)-cyclopentanone
2-(6-carboxyhexyl)-3-(2-hydroxy-2-methyl-3-phenylpropylthio)-cyclopentanone
2-(6-carboxyhexyl)-3-(2-hydroxy-2-methyl-5-phenylpentylthio)-cyclopentanone
2-(6-carboxyhexyl)-3-(2-hydroxy-3,3-dimethyl-3-phenylpropylthio)-cyclopentanone
2-(6-carboxyhexyl)-3-(2-hydroxy-3,3-dimethyl-5-phenylpentylthio)-cyclopentanone
2-(6-carboxyhexyl)-3-(2-hydroxy-2,3,3-trimethyl-3-phenylpropylthio)-cyclopentanone
2-(6-carboxyhexyl)-3-(2-hydroxy-2,3,3-trimethyl-5-phenylpentylthio)-cyclopentanone
2-(6-carbethoxyhexyl)-3-heptylthio-cyclopentanone
2-(6-carbethoxyhexyl)-3-(2-hydroxyheptylthio)-cyclopentanone
2-(6-carbethoxyhexyl)-3-(2-hydroxynonylthio)-cyclopentanone
2-(6-carbethoxyhexyl)-3-(2-hydroxy-2-methylheptylthio)-cyclopentanone
2-(6-carbethoxyhexyl)-3-(2-hydroxy-2-methylnonylthio)-cyclopentanone
2-(6-carbethoxyhexyl)-3-(2-hydroxy-3,3-dimethylheptylthio)-cyclopentanone
2-(6-carbethoxyhexyl)-3-(2-hydroxy-3,3-dimethylnonylthio)-cyclopentanone
2-(6-carbethoxyhexyl)-3-(2-hydroxy-6,6-dimethylheptylthio)-cyclopentanone
2-(6-carbethoxyhexyl)-3-(2-hydroxy-8,8-dimethylnonylthio)-cyclopentanone
2-(6-carbethoxyhexyl)-3-(2-hydroxy-2,3,3-trimethylheptylthio)-cyclopentanone
2-(6-carbethoxyhexyl)-3-(2-hydroxy-2,3,3-trimethylnonylthio)-cyclopentanone
2-(6-carbethoxyhexyl)-3-(2-hydroxy-2,6,6-trimethylheptylthio)-cyclopentanone
2-(6-carbethoxyhexyl)-3-(2-hydroxy-2,8,8-trimethylnonylthio)-cyclopentanone
2-(6-carbethoxyhexyl)-3-(2-hydroxy-7,7,7-trifluoroheptylthio)-cyclopentanone
2-(6-carbethoxyhexyl)-3-(2-hydroxy-9,9,9-trifluorononylthio)-cyclopentanone
2-(6-carbethoxyhexyl)-3-(2-hydroxy-2-methyl-7,7,7-trifluoroheptylthio)-cyclopentanone
2-(6-carbethoxyhexyl)-3-(2-hydroxy-2-methyl-9,9,9-trifluorononylthio)-cyclopentanone
2-(6-carbethoxyhexyl)-3-(2-hydroxy-3,3-dimethyl-7,7,7-trifluoroheptylthio)-cyclopentanone
2-(6-carbethoxyhexyl)-3-(2-hydroxy-3,3-dimethyl-9,9,9-trifluorononylthio)-cyclopentanone
2-(6-carbethoxyhexyl)-3-(2-hydroxy-2,3,3-trimethyl-7,7,7-trifluoroheptylthio)-cyclopentanone
2-(6-carbethoxyhexyl)-3-(2-hydroxy-2,3,3-trimethyl-9,9,9-trifluorononylthio)-cyclopentanone
2-(6-carbethoxyhexyl)-3-(2-hydroxy-3-phenylpropylthio)-cyclopentanone
2-(6-carbethoxyhexyl)-3-(2-hydroxy-5-phenylpentylthio)-cyclopentanone
2-(6-carbethoxyhexyl)-3-(2-hydroxy-2-methyl-3-phenylpropylthio)-cyclopentanone
2-(6-carbethoxyhexyl)-3-(2hydroxy-2-methyl-5-phenylpentylthio)-cyclopentanone
2-(6-carbethoxyhexyl)-3-(2-hydroxy-3,3-dimethyl-3-phenylpropylthio)-cyclopentanone
2-(6-carbethoxyhexyl)-3-(2-hydroxy-3,3-dimethyl-5-phenylpentylthio)-cyclopentanone
2-(6-carbethoxyhexyl)-3-(2-hydroxy-2,3,3-trimethyl-3-phenylpropylthio)-cyclopentanone
2-(6-carbethoxyhexyl)-3-(2-hydroxy-2,3,3-trimethyl-5-phenylpentylthio)-cyclopentanone
2-(6-carbodecyloxyhexyl)-3-heptylthio-cyclopentanone
2-(6-carbodecyloxyhexyl)-3-(2-hydroxyheptylthio)-cyclopentanone
2-(6-carbodecyloxyhexyl)-3-(2-hydroxynonylthio)-cyclopentanone
2-(6-carbodecyloxyhexyl)-3-(2-hydroxy-2-methylheptylthio)-cyclopentanone
2-(6-carbodecyloxyhexyl)-3-(2-hydroxy-2-methylnonylthio)-cyclopentanone
2-(6-carbodecyloxyhexyl)-3-(2-hydroxy-3,3-dimethylheptylthio)-cyclopentanone
2-(6-carbodecyloxyhexyl)-3-(2-hydroxy-3,3-dimethylnonylthio)-cyclopentanone
2-(6-carbodecyloxyhexyl)3-(2-hydroxy-6,6-dimethylheptylthio)-cyclopentanone
2-(6-carbodecyloxyhexyl)-3-(2-hydroxy-8,8-dimethylnonylthio)-cyclopentanone
2-(6-carbodecyloxyhexyl)-3-(2-hydroxy-2,3,3-trimethylheptylthio)-cyclopentanone
2-(6-carbodecyloxyhexyl)-3-(2-hydroxy-2,3,3-trimethylnonylthio)-cyclopentanone
2-(6-carbodecyloxyhexyl)-3-(2-hydroxy-2,6,6-trimethylheptylthio)-cyclopentanone
2-(6-carbodecyloxyhexyl)-3-(2-hydroxy-2,8,8-trimethylnonylthio)-cyclopentanone
2-(6-carbodecyloxyhexyl)-3-(2-hydroxy-7,7,7-trifluoroheptylthio)-cyclopentanone
2-(6-carbodecyloxyhexyl)-3-(2-hydroxy-9,9,9-trifluorononylthio)-cyclopentanone
2-(6-carbodecyloxyhexyl)3-(2-hydroxy-2-methyl-7,7,7-trifluoroheptylthio)-cyclopentanone
2-(6-carbodecyloxyhexyl)-3-(2-hydroxy-2-methyl-9,9,9-trifluorononylthio)-cyclopentanone
2-(6-carbodecyloxyhexyl)-3-(2-hydroxy-3,3-dimethyl-7,7,7-trifluoroheptylthio)-cyclopentanone
2-(6-carbodecyloxyhexyl)-3-(2-hydroxy-3,3-dimethyl-9,9,9-trifluorononylthio)-cyclopentanone
2-(6-carbodecyloxyhexyl)-3-(2-hydroxy-2,3,3-trimethyl-7,7,7-trifluoroheptylthio)-cyclopentanone
2-(6-carbodecyloxyhexyl)-3-(2-hydroxy-2,3,3-trimethyl-9,9,9-trifluorononylthio)-cyclopentanone
2-(6-carbodecyloxyhexyl)-3-(2-hydroxy-3-phenylpropylthio)-cyclopentanone
2-(6carbodecyloxyhexyl)-3-(2-hydroxy-5-phenylpentylthio)-cyclopentanone
2-(6-carbodecyloxyhexyl)-3-(2-hydroxy-2-methyl-3-phenylpropylthio)-cyclopentanone
2-(6-carbodecyloxyhexyl)-3-(2-hydroxy-2-methyl-5-phenylpentylthio)-cyclopentanone
2-(6-carbodecyloxyhexyl)-3-(2-hydroxy-3,3-dimethyl-3-phenylpropylthio)-cyclopentanone
2-(6-carbodecyloxyhexyl)-3-(2-hydroxy-3,3-dimethyl-5-phenylpentylthio)-cyclopentanone
2-(6-carbodecyloxyhexyl)-3-(2-hydroxy-2,3,3-trimethyl-3-phenylpropylthio)-cyclopentanone 2-(6-carbodecyloxyhexyl)-3-(2-hydroxy-2,3,3-trimethyl-5-phenylpentylthio)-cyclopentanone, the final products set forth below are obtained by reaction with NaBH₄:

2-(6-carboxyhexyl)-3-(2-hydroxyheptylthio)-cyclopentanol
2-(6-carboxyhexyl)-3-(2-hydroxynonylthio)-cyclopentanol
2-(6-carboxyhexyl)-3-(2-hydroxy-2-methylheptylthio)-cyclopentanol
2-(6-carboxyhexyl)-3-(2-methylnonylthio)-cyclopentanol
2-(6-carboxyhexyl)-3-(2-hydroxy-3,3-dimethylheptylthio)-cyclopentanol
2-(6-carboxyhexyl)-3-(2-hydroxy-3,3-dimethylnonylthio)-cyclopentanol
2-(6-carboxyhexyl)-3-(2-hydroxy-6,6-dimethylheptylthio)-cyclopentanol
2-(6-carboxyhexyl)-3-(2-hydroxy-8,8-dimethylnonylthio)-cyclopentanol
2-(6-carboxyhexyl)-3-(2-hydroxy-2,3,3-trimethylheptylthio)-cyclopentanol
2-(6-carboxyhexyl)-3-(2-hydroxy-2,3,3-trimethylnonylthio)-cyclopentanol
2-(6-carboxyhexyl)-3-(2-hydroxy-2,6,6-trimethylheptylthio)-cyclopentanol
2-(6-carboxyhexyl)-3-(2-hydroxy-2,8,8-trimethylnonylthio)-cyclopentanol
2-(6-carboxyhexyl)-3-(2-hydroxy-7,7,7-trifluoroheptylthio)-cyclopentanol
2-(6-carboxyhexyl)-3-(2-hydroxy-9,9,9-trifluorononylthio)-cyclopentanol
2-(6-carboxyhexyl)-3-(2-hydroxy-2-methyl-7,7,7-trifluoroheptylthio)-cyclopentanol
2-(6-carboxyhexyl)-3-(2-hydroxy-2-methyl-9,9,9-trifluorononylthio)-cyclopentanol
2-(6-carboxyhexyl)-3-(2-hydroxy-3,3-dimethyl-7,7,7-trifluoroheptylthio)-cyclopentanol
2-(6-carboxyhexyl)-3-(2-hydroxy-3,3-dimethyl-9,9,9-trifluorononylthio)-cyclopentanol
2-(6-carboxyhexyl)-3-(2-hydroxy-2,3,3-trimethyl-7,7,7-trifluoroheptylthio)-cyclopentanol
2-(6-carboxyhexyl)-3-(2-hydroxy-2,3,3-trimethyl-9,9,9-trifluorononylthio)-cyclopentanol
2-(6-carboxyhexyl)-3-(2-hydroxy-3-phenylpropylthio)-cyclopentanol
2-(6-carboxyhexyl)-3-(2-hydroxy-5-phenylpentylthio)-cyclopentanol
2-(6-carboxyhexyl)-3-(2-hydroxy-2-methyl-3-phenylpropylthio)-cyclopentanol
2-(6-carboxyhexyl)-3-(2-hydroxy-2-methyl-5-phenylpentylthio)-cyclopentanol
2-(6-carboxyhexyl)-3-(2-hydroxy-3,3-dimethyl-3-phenylpropylthio)-cyclopentanol
2-(6-carboxyhexyl)-3-(2-hydroxy-3,3-dimethyl-5-phenylpentylthio)-cyclopentanol
2-(6-carboxyhexyl)-3-(2-hydroxy-2,3,3-trimethyl-3-phenylpropylthio)-cyclopentanol
2-(6-carboxyhexyl)-3-(2-hydroxy-2,3,3-trimethyl-5-phenylpentylthio)-cyclopentanol
2-(6-carbethoxyhexyl)-3-heptylthio-cyclopentanol
2-(6-carbethoxyhexyl)-3-(2-hydroxyheptylthio)-cyclopentanol
2-(6-carbethoxyhexyl)-3-(2-hydroxynonylthio)-cyclopentanol
2-(6-carbethoxyhexyl)-3-(2-hydroxy-2-methylheptylthio)-cyclopentanol
2-(6-carbethoxyhexyl)-3-(2-hydroxy-2-methylnonylthio)-cyclopentanol
2-(6-carbethoxyhexyl)-3-(2-hydroxy-3,3-dimethylheptylthio)-cyclopentanol
2-(6-carbethoxyhexyl)-3-(2-hydroxy-3,3-dimethylnonylthio)-cyclopentanol
2-(6-carbethoxyhexyl)-3-(2-hydroxy-6,6-dimethylheptylthio)-cyclopentanol
2-(6-carbethoxyhexyl)-3-(2-hydroxy-8,8-dimethylnonylthio)-cyclopentanol
2-(6-carbethoxyhexyl)-3-(2-hydroxy-2,3,3-trimethylheptylthio)-cyclopentanol
2-(6-carbethoxyhexyl)-3-(2-hydroxy-2,3,3-trimethylnonylthio)-cyclopentanol
2-(6-carbethoxyhexyl)-3-(2-hydroxy-2,6,6-trimethylheptylthio)-cyclopentanol
2-(6-carbethoxyhexyl)-3-(2-hydroxy-2,8,8-trimethylnonylthio)-cyclopentanol
2-(6-carbethoxyhexyl)-3-(2-hydroxy-7,7,7-trifluoroheptylthio)-cyclopentanol
2-(6-carbethoxyhexyl)-3-(2-hydroxy-9,9,9-trifluorononylthio)-cyclopentanol
2-(6-carbethoxyhexyl)-3-(2-hydroxy-2-methyl7,7,7-trifluoroheptylthio)-cyclopentanol
2-(6-carbethoxyhexyl)-3-(2-hydroxy-2-methyl-9,9,9-trifluorononylthio)-cyclopentanol
2-(6-carbethoxyhexyl)-3-(2-hydroxy-3,3-dimethyl-7,7,7-trifluoroheptylthio)-cyclopentanol
2-(6-carbethoxyhexyl-3-(2-hydroxy-3,3-dimethyl-9,9,9-trifluorononylthio)-cyclopentanol
2-(6-carbethoxyhexyl)-3-(2-hydroxy-2,3,3-trimethyl-7,7,7-trifluoroheptylthio)-cyclopentanol
2-(6-carbethoxyhexyl)-3-(2-hydroxy-2,3,3-trimethyl-9,9,9-trifluorononylthio)-cyclopentanol
2-(6-carbethoxyhexyl)-3-(2-hydroxy-3-phenylpropylthio)-cyclopentanol
2-(6-carboethoxyhexyl)-3-(2-hydroxy-5-phenylpentylthio)-cyclopentanol
2-(6-carbethoxyhexyl)-3-(2-hydroxy-2-methyl-3-phenylpropylthio)-cyclopentanol
2-(6-carbethoxyhexyl)-3-(2-hydroxy-2-methyl-5-phenylpentylthio)-cyclopentanol
2-(6-carbethoxyhexyl)-3-(2-hydroxy-3,3-dimethyl-3-phenylpropylthio)-cyclopentanol
2-(6-carbethoxyhexyl)-3-(2-hydroxy-3,3-dimethyl-5-phenylpentylthio)-cyclopentanol
2-(6-carbethoxyhexyl)-3-(2-hydroxy-2,3,3-trimethyl-3-phenylpropylthio)-cyclopentanol
2-(6-carbethoxyhexyl)-3-(2-hydroxy-2,3,3-trimethyl-5-phenylpentylthio)-cyclopentanol
2-(6-carbodecyloxyhexyl)-3-heptylthio-cyclopentanol
2-(6-carbodecyloxyhexyl)-3-(2-hydroxyheptylthio)-cyclopentanol
2-(6-carbodecycloxyhexyl)-3-(2-hydroxynonylthio)-cyclopentanol
2-(6-carbodecyloxyhexyl)-3-(2-hydroxy-2-methyl-hepthlthio)-cyclopentanol
2-(6-carbodecyloxyhexyl)-3-(2-hydroxy-2-methyl-nonylthio)-cyclopentanol
2-(6-carbodecyloxyhexyl)-3-(2-hydroxy-3,3-dimethylheptylthio)-cyclopentanol
2-(6-carbodecyloxyhexyl)-3-(2-hydroxy-3,3-dimethylnonylthio)-cyclopentanol
2-(6-carbodecyloxyhexyl)-3-(2-hydroxy-6,6-dimethylheptylthio)-cyclopentanol
2-(6-carbodecyloxyhexyl)-3-(2-hydroxy-8,8-dimethylnonylthio)-cyclopentanol 2-(6-carbodecyloxyhexyl)-3-(2-hydroxy-2,3,3-trimethylheptylthio)-cyclopentanol
2-(6-carbodecyloxyhexyl)-3-(2-hydroxy-2,3,3-trimethylnonylthio)-cyclopentanol
2-(6-carbodecyloxyhexyl)-3-(2-hydroxy-2,6,6-trimethylheptylthio)-cyclopentanol
2-(6-carbodecyloxyhexyl)-3-(2-hydroxy-2,8,8-trimethylnonylthio)-cyclopentanol
2-(6-carbodecyloxyhexyl)-3-(2-hydroxy-7,7,7-trifluoroheptylthio)-cyclopentanol
2-(6-carbodecyloxyhexyl)-3-(2-hydroxy-9,9,9-trifluorononylthio)-cyclopentanol
2-(6-carbodecyloxyhexyl)-3-(2-hydroxy-2-methyl-7,7,7-trifluoroheptylthio)-cyclopentanol
2-(6-carbodecyloxyhexyl)-3-(2-hydroxy-2-methyl-9,9,9-trifluorononylthio)-cyclopentanol
2-(6-carbodecyloxy-hexyl)-3-(2-hydroxy-3,3-dimethyl-7,7,7-trifluoroheptylthio)-cyclopentanol
2-(6-carbodecyloxyhexyl)-3-(2-hydroxy-3,3-dimethyl-9,9,9-trifluorononylthio)-cyclopentanol
2-(6-carbodecyloxyhexyl)3-(2-hydroxy-2,3,3-trimethyl-7,7,7-trifluoroheptylthio)-cyclopentanol
2-(6-carbodecyloxyhexyl)-3-(2-hydroxy-2,3,3-trimethyl-9,9,9-trifluoronylthio)-cyclopentanol
2-(6-carbodecyloxyhexyl)-3-(2-hydroxy-3-phenylpropylthio)-cyclopentanol
2-(6-carbodecyloxyhexyl)-3-(2-hydroxy-5-phenylpentylthio)-cyclopentanol
2-(6-carbodecyloxyhexyl)-3-(2-hydroxy-2-methyl-3-phenylpropylthio)-cyclopentanol
2-(6-carbodecyloxyhexyl)-3-(2-hydroxy-2-methyl-5-phenylpentylthio)-cyclopentanol
2-(6-carbodecyloxyhexyl)-3-(2-hydroxy-3,3-dimethyl-3-phenylpropylthio)-cyclopentanol
2-(6-carbodecyloxyhexyl)-3-(2-hydroxy-3,3-dimethyl-5-phenylpentylthio)-cyclopentanol
2-(6-carbodecyloxyhexyl)-3-(2-hydroxy-2,3,3-trimethyl-3-phenylpropylthio)-cyclopentanol
2-(6-carbodecyloxyhexyl)-3-(2-hydroxy-2,3,3-trimethyl-5-phenylpentylthio)-cyclopentanol.

EXAMPLE 11

4.7 g. of 1,1-ethylenedioxy-2-(6-tert.-butoxycarbonylhexyl)-3-(2-hydroxy-2-methylheptylthio)-cyclopentane (obtainable from 2-(6-carboxyhexyl)-2-cyclopentenone, addition of 2-hydroxyheptanethiol, subsequent ketalization with ethylene glycol, as well as oxidation with $CrO_3$ in ether, addition to isobutylene, and reaction of the thus-obtained 1,1-ethylenedioxy-2-(6-tert.-butoxycarbonylhexyl)-3-(2-oxoheptylthio)-cyclopentane with methylmagnesium bromide) is agitated for 2 hours at room temperature in 60 ml. of 2N aqueous HCl, extracted, after cooling, three times with $CH_2Cl_2$; the organic phase is washed with water, dried over $Na_2SO_4$, the solvent is distilled off, and chromatographic purification of the residue (silica gel/chloroform) yields 2-(6-carboxyhexyl)-3-(2-hydroxy-2-methylheptylthio)-cyclopentanone. $R_f$ = 0.25 (silica gel/chloroform : methanol = 95 : 5).

| Analysis: | C | H | S |
|---|---|---|---|
| Calculated: | 64.48 % | 9.74 % | 8.61 % |
| Found: | 65.6 % | 10.7 % | 7.9 % |

IR spectrum: bands at 1705, 1740, 2850, 2920, and 3400 cm$^{-1}$; broad band between 3000 and 3300 cm$^{-1}$.

NMR spectrum: signals at 0.9 p.p.m., 2.75 p.p.m., 3.0 p.p.m., and 6.4 p.p.m.

EXAMPLE 12

At room temperature, 70 ml. of a 0.2N diazoethane solution in ether is added to a solution of 3.4 g. of 2-(6-carboxyhexyl)-3-heptylthio-cyclopentanone in 25 ml. of dry ethanol. The reaction mixture is poured into 100 ml. of ice water, containing 5 ml. of concentrated HCl, agitated, the organic phase separated, the aqueous phase extracted three times with respectively 30 ml. of chloroform, and the combined organic phases are washed with water, dried over $Na_2SO_4$, the solvent is distilled off, and chromatographic purification of the residue (silica gel/chloroform) produces 2-(6-carbethoxyhexyl)-3-heptylthio-cyclopentanone. $R_f$ = 0.7 (silica gel/chloroform).

| Analysis: | C | H | S |
|---|---|---|---|
| Calculated: | 68.07 % | 10.33 % | 8.65 % |
| Found: | 67.8 % | 10.4 % | 8.6 % |

IR spectrum: bands at 1730, 2870, and 2950 cm$^{-1}$.
NMR spectrum: signals at 0.9 p.p.m., 3.0 p.p.m., and between 3.95 and 4.3 p.p.m. (quartet).

EXAMPLE 13

(a) Analogously to Example 1 2-(6-carboxyhexyl)-3-(2-hydroxy-2-p-tolylethylthio)-cyclopentanone,
IR spectrum: bands at 1500, 1620, 1700, and 1735 cm$^{-1}$,
broad band at 3500 cm$^{-1}$,
NMR spectrum: signals at 2.3 p.p.m. (singulet),
2.88 p.p.m., 4.79 p.p.m. (triplet), and between 7.2 and 7.35 p.p.m. (multiplet) is obtained as an oil by reacting
2-(6-carboxyhexyl)-2-cyclopentenone with
2-hydroxy-2-p-toly-ethanethiol (obtainable from 4-methylbenzaldehyde analogously as described in Example A); and
2-(6-carboxyhexyl)-3-(2-hydroxy-2-methyl-2-p-tolylethylthio)-cyclopentanone,
IR spectrum: bands at 1500, 1620, 1700, 1740 cm$^{-1}$,
broad band at 3400 cm$^{-1}$,
NMR spectrum: signals at 1.55 p.p.m. (singulet),
2.3 p.p.m. (singulet), and between 7.0 and 7.3 p.p.m. (multiplet) is obtained as an oil by reacting 2-(6-carboxyhexyl)-2-cyclopentenone with
2-hydroxy-2-methyl-2-p-toly-ethanethiol (obtainable from 4-methylacetaphenone analogously as described in Example A).

(b) Analogously to Example 1, with the use of the following starting compounds
2-hydroxy-2-methylheptanethiol
2-hydroxy-2-methyl-2-p-tolylethanethiol
2-hydroxy-2-p-tolylethanethiol
2-hydroxy-2-methyl-3-phenylpropanethiol the final products set forth below are obtained as an oil by reaction with 2-(6-carboxyhexyl)-4-hydroxy-2-cyclopentenone 2-(6-carboxyhexyl)-3-(2-hydroxy-2-methyl-heptylthio)-4-hydroxycyclopentanone,
IR spectrum: bands at 1710 and 1740 cm$^{-1}$,
broad band at 3450 cm$^{-1}$,
NMR spectrum: signals at 0.85 p.p.m., 1.2 p.p.m., 2.3 p.p.m. (triplet), 4.2 p.p.m. and 5.8 p.p.m. (multiplet); and a stereoisomer of this compound an an oil, IR spectrum: bands at 1710 and 1740 cm$^{-1}$, broad band at 3500 cm$^{-1}$;

NMR spectrum: signals at 0.86 p.p.m., 1.2 p.p.m., 2.31 p.p.m. (triplet), 4.2 p.p.m. and 5.75 p.p.m. (multiplet);

2-(6-carboxyhexyl)-3-(2-hydroxy-2-methyl-2-p-tolyethylthio)-4-hydroxy-cyclopentanone as an oil IR spectrum: bands at 1510, 1707 and 1740 cm$^{-1}$, broad band 3400 cm$^{-1}$, NMR spectrum: signals at 1.6 p.p.m. (singulet), 2.3 p.p.m. (singulet), 4.2 p.p.m. and between 7.1 and 7.5 p.p.m. (multiplet);

and a stereoisomer of this compound as an oil,

IR spectrum: bands at 1506, 1705 and 1740 cm$^{-1}$, broad band at 3420 cm$^{-1}$, NMR spectrum: signals at 1.6 p.p.m. (singulet), 2.32 p.p.m. (singulet), 4.25 p.p.m. and between 7.1 and 7.5 p.p.m. (multiplet);

2-(6-carboxyhexyl)-3-(2-hydroxy-2-p-tolylethylthio)-4-hydroxycyclopentanone as an oil;

2-(6-carboxyhexyl)-3-(2-hydroxy-2-methyl-3-phenyl-propylthio)-4-hydroxy-cyclopentanone as an oil, IR spectrum: bands at 1500, 1715 and 1745 cm$^{-1}$, broad hand at 3450 cm$^{-1}$, NMR spectrum: signals at 1.2 p.p.m., 2.35 p.p.m. (triplet) 5 p.p.m. (broad multiplet) and 7.3 p.p.m.;

and a stereoisomer of this compound as an oil,

IR spectrum: bands at 1600, 1745 and 1750 cm$^{-1}$, broad band at 3400 cm$^{-1}$, NMR spectrum: signals at 1.2 p.p.m., 2.25 p.p.m. (triplet) 4.25 p.p.m., 5.2 p.p.m. (broad multiplet) and 7.3 p.p.m.

(c) 2 g of 2-(6-carboxyhexyl)-3-(2-hydroxy-2-methyl-2-p-tolylethylthio)-4-hydroxy-cyclopentanone is dissolved in 50 ml methanol, two drops of water are added and with cooling by ice and agitating 1.5 g NaBH$_4$ is added during 2 hours. After addition of 50 ml ice-water the mixture is acidified with aqueous HCl and extracted three times with respectively 50 ml portions of dimethylether. The combined organic phases are washed three times with a saturated aqueous NaCl-solution, dried over Na$_2$SO$_4$, filtered and evaporated. After chromatographic purification of the residue (silica gel/chloroform : methanol = 9 : 1) 2-(6-carboxyhexyl-3-(2-hydroxy-2-methyl-2-p-tolylethylthio)-1,4-cyclopentanediol is obtained as an oil, IR spectrum: bands at 1505 and 1705 cm$^{-1}$, broad band at 3350 cm$^{-1}$, NMR spectrum: signals at 1.23 p.p.m., 2.3 p.p.m., 4.21 p.p.m. (quartet), 4.6 p.p.m. (broad multiplet) and between 7.0 and 7.3 p.p.m.

2-(6-carboxyhexyl)-3-(2-hydroxy-2-methylheptylthio)-1,4-cyclopentanediol is obtained analogously as an oil by reduction of 2-(6-carboxyhexyl)-3-(2-hydroxy-2-methylheptythio)-4-hydroxy-cyclopentanone with NaBH$_4$.

EXAMPLE 14

2.0 g. of acetic anhydride, dissolved in 20 ml. of pyridine, is added to a solution of 3.9 g. of 2-(6-carbethoxyhexyl)-3-(2-hydroxyhepthylthio)-cyclopentanone in 30 ml. of pyridine. The reaction mixture is agitated for 14 hours at 25°, the reaction mixture is poured into 100 ml. of water, saturated with NaCl, extracted three times with respectivity 40 ml. of ether, and the organic phase is washed with water, dried over Na$_2$SO$_4$, the solvent is distilled off, and chromatographic purification of the residue (silica gel/chloroform) yields 2-(6-carbethoxyhexyl)-3-(2-acetoxyheptylthio)-cyclopentanone.

EXAMPLE 15

Analogously to Example 13, with the use of the following starting compounds:

2-(6-carbethoxyhexyl)-3-heptylthio-cyclopentanol 2-(6-carbethoxyhexyl)-3-(2-hydroxy-2-methylheptylthio)-cyclopentanol 2-(6-carbethoxyhexyl)-3-(2-hydroxy-2-methylnonylthio)-cyclopentanol 2-(6-carbethoxyhexyl)-3-(2-hydroxy-3,3-dimethylheptylthio)-cyclopentanol 2-(6-carbethoxyhexyl)-3-(2-hydroxy-3,3-dimethylnonylthio)-cyclopentanol, the final products set forth below are obtained by reaction with acetic anhydride in pyridine:

2-(6-carbethoxyhexyl)-3-heptylthio-cyclopentyl acetate

2(6-carbethoxyhexyl)-3-(2-acetoxy-2-methylheptylthio)-cyclopentyl acetate 2-(6-carbethoxyhexyl)-3-(2-acetoxy-2methylnonylthio)-cyclopentyl acetate 2-(6-carbethoxyhexyl)-3-(2-acetoxy-3,3-dimethylheptylthio)-cyclopentyl acetate 2-(6-carboxyhexyl)-3-(2-acetoxy-3,3-dimethylnonylthio)-cyclopentyl acetate.

EXAMPLE 16

0.24 g. of sodium is dissolved in 20 ml. of dry ethanol; a solution of 3.4 g. of 2-(6-carboxyhexyl)-2-heptylthio-cyclopentanone in 20 ml. of dry ethanol is added dropwise thereto, and the reaction mixture is diluted with 60 ml. of dry ether. The thus-precipitated sodium salt of 2-(6-carboxyhexyl)-2-heptylthio-cyclopentanone is filtered off.

EXAMPLE 17

10 ml. of 1N aqueous HCl is added to a solution of 3.7 g. of the sodium salt of 2-(6-carboxyhexyl)-2-heptylthio-cyclopentanone in a mixture of 30 ml. of water and 30 ml. of ethanol; the reaction mixture is saturated with NaCl, extracted three times with respectively 20 ml. of benzene, the organic phase washed with water, dried over Na$_2$SO$_4$, the solvent is distilled off, and chromatographic purification of the residue (silica gel/chloroform) yields 2-(6-carboxyhexyl)-3-heptylthio-cyclopentanone.

$R_f = 0.3$ (silica gel/chloroform : methanol = 95 : 5).

| Analysis: | C | H | S |
|---|---|---|---|
| Calculated: | 66.62 % | 10.01 % | 9.36 % |
| Found: | 65.5 % | 9.71 % | 9.8 % |

IR spectrum: bands at 1700, 1730, 2860, and 2940 cm$^{-1}$; broad band between 3000 and 3400 cm$^{-1}$.

NMR spectrum: signals at 0.86 p.p.m., 3.0 p.p.m., and 9.75 p.p.m.

The following Examples A and B describe the preparation of several of the starting substances employed according to the present invention:

EXAMPLE A 20 g. of a 20% sodium hydride dispersion in paraffin oil is washed three times with 30 ml. of dry n-pentane. The sovlent is removed, and 33 g. of trimethylsulfoxonium iodide is added. Then, 100 ml. of dimethyl sulfoxide is introduced dropwise, the mixture is agitated for 20 minutes at room temperature until the evolution of gas is terminated, and a solution of 14.2 g. of 2-heptanone in 15 ml. of dimethyl sulfoxide is added dropwise thereto. The mixture is then stirred for another 2 hours; under ice cooling, 500 ml. of water is added, the mixture extracted three times with respectively 250 ml. of ether; the combined ether extracts are washed with water, dried with sodium sulfate, and the solvent is distilled off. After fractionation of the residue, 2-methyl-2-pentyloxirane is obtained as colorless liquid; b.p. = 55° (20 mm. Hg).

Under ice cooling, hydrogen sulfide is introduced into 150 ml. of methanol under agitation until the weight gain amounts to 3.2 g. Then, a solution of 370 mg. of diethylamine in 11 ml. of methanol is added thereto, and thereafter 4.8 g. of 2-methyl-2-pentyloxirane in 18 ml. of methanol is introduced into the reaction mixture. Hydrogen sulfide gas is again added to the solution for 15 minutes, then the solution is allowed to stand at room temperature for 12 hours, the solvent is distilled off, and the residue is dissolved in 50 ml. of petroleum ether (b.p. = 50°–70°), washed with water, dried with sodium sulfate, the solvent distilled off, and the residue thus produced is 2-hydroxy-2-methyl-heptanethiol as a colorless liquid.

| Analysis: | C | H | S |
|---|---|---|---|
| Calculated: | 59.2 % | 11.18 % | 19.76 % |
| Found: | 60.1 % | 11.6 % | 20.2 % |

IR spectrum: bands at 920, 1140, 1380, 1465, 2570, and 3450 cm$^{-1}$.

NMR spectrum: signals at 0.96 p.p.m., 1.26 p.p.m., 2.27 p.p.m., and 2.67 p.p.m.

Analogously, other 2-hydroxy-2-methyl-R$_4$-sulfides of Formula II can also be produced from the corresponding ketones, especially those disclosed in Examples 1 and 2.

EXAMPLE B

Under agitation, 500 g. of potassium salt of the ethyl ester of 2-oxocyclopentanecarboxylic acid is added to a boiling solution of 550 g. of the ethyl ester of 7-bromoenanthic acid in 6 l. of toluene; the mixture is further refluxed and, after one hour, another 250 g. of the potassium salt of the ethyl ester of 2-oxocyclopentanecarboxylic acid is added thereto. The reaction mixture is refluxed for another 24 hours, filtered after cooling, the solvent is distilled off, the residue is diluted with 3 l. of ether, washed with water, dried over Na$_2$SO$_4$, and the solvent is distilled off. After fractionation of the residue, 2-carbethoxy-2-(6-carbethoxyhexyl)-cyclopentanone is obtained as a colorless oil, b.p. = 165° (0.3 mm. Hg).

Under agitation at 20°, 48 g. of Br$_2$, dissolved in 500 ml. of CHCl$_3$, is added dropwise within 2 hours to a solution of 100 g. of 2-carbethoxy-2-(6-carbethoxyhexyl)-cyclopentanone in 1 l. of CHCl$_3$. The solvent is distilled off, the residue is taken up in a mixture of 4 l. of ethanol, 1 kg. of H$_2$SO$_4$ (density: 1.84), and 100 ml. of H$_2$O, refluxed for 18 hours under N$_2$ and poured on 10 kg. of ice after cooling. The reaction mixture is extracted three times with respectively 5 l. of ether, the combined ether extracts are dried over Na$_2$SO$_4$, the solvent is distilled off, and chromatographic purification of the residue (silica gel/petroleum ether : ether =1 : 1) yields 2-(6-carbethoxyhexyl)-2-cyclopentenone.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compounds of the formula

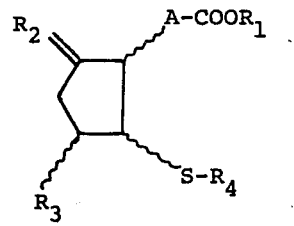

wherein R$_1$ is H or alkyl of up to 12 carbon atoms; R$_2$ is =O, (H,OH) or (H,acyloxy) wherein acyloxy is alkanoyloxy or alkanesulfonyloxy each of up to 4 carbon atoms; R$_3$ is H, OH or acyloxy as defined above; R$_4$ is alkyl, fluoroalkyl, 2-hydroxyalkyl or 2-acyloxyalkyl wherein acyloxy is as defined above, each alkyl being of 2 of 12 carbon atoms which is unsubstituted or substituted by phenyl of p-tolyl; and A is alkylene of 4 to 8 carbon atoms which is unsubstituted or substituted by F, and the physiologically acceptable salts thereof.

2. A compound of claim 1 wherein R$_3$ is H.
3. A compound of claim 1 wherein R$_3$ is OH.
4. A compound of claim 1 wherein A is hexamethylene.
5. A compound of claim 1 wherein R$_1$ is H or alkyl of 1–6 carbon atoms.
6. A compound of claim 1 wherein R$_2$ is =O or H,OH.
7. A compound of claim 1 wherein A is hexamethylene; R$_1$ is H or straight chain alkyl of 1 to 6 carbon atoms, R$_2$ is=O or H,OH; R$_3$ is H or OH; and R$_4$ is 2-hydroxyalkyl of 2 to 12 carbon atoms or a corresponding group substituted by p-tolyl in the ω-position.
8. A compound of claim 7 wherein R$_3$ is OH.
9. A compound of claim 1, 2-(6-carboxyhexyl)-3-heptylthio-cyclopentanone.
10. A compound of claim 1, 2-(6-carbethoxyhexyl)-3-heptylthio-cyclopentanone.
11. A compound of claim 1, 2-(6-carboxyhexyl)-3-(2-hydroxyheptylthio)-cyclopentanone.
12. A compound of claim 1, 2-(6-carboxyhexyl)-3-heptylthio-cyclopentanol-(1β).
13. A compound of claim 1, 2-(6-carboxyhexyl)-3-(2-hydroxy-2-methylheptylthio)-cyclopentanone.
14. A compound of claim 1, 2-(6-carboxyhexyl)-3-(2-hydroxy-2-p-tolylethylthio)-cyclopentanone.
15. A compound of claim 1, 2-(6-carboxyhexyl)-3-(2-hydroxy-2-methyl-2-p-tolylethylthio)-cyclopentanone.
16. A compound of claim 1, 2-(6-carboxyhexyl)-3-(2-hydroxy-2-methylheptylthio)-4-hydroxy-cyclopentanone.

17. A compound of claim 1, 2-(6-carboxyhexyl)-3-(2-hydroxy-2-methyl-2-p-tolylethylthio)-4-hydroxy-cyclopentanone.

18. A compound of claim 1, 2-(6-carboxyhexyl)-3-(2-hydroxy-2-methyl-3-phenylpropylthio-4-hydroxy-cyclo pentanone.

19. A compound of claim 1, 2-(6-carboxyhexyl)-3-(2-hydroxy-2-methyl-2-p-tolylethylthio)-1,4-cyclopentanediol.

* * * * *